(12) United States Patent
Khine et al.

(10) Patent No.: US 10,898,084 B2
(45) Date of Patent: Jan. 26, 2021

(54) VITAL SIGNS MONITOR

(71) Applicant: The Regents of the University of California, Oakland, CA (US)

(72) Inventors: Michelle Khine, Irvine, CA (US); Nicole Eckmann, Folsom, CA (US); Kimberly Veliz, Paramount, CA (US); Jonathan Pegan, Irvine, CA (US); Joshua Kim, Irvine, CA (US); Sun-Jun Park, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 468 days.

(21) Appl. No.: 15/474,937

(22) Filed: Mar. 30, 2017

(65) Prior Publication Data

US 2017/0281082 A1     Oct. 5, 2017

Related U.S. Application Data

(60) Provisional application No. 62/316,375, filed on Mar. 31, 2016.

(51) Int. Cl.
 *A61B 5/021* (2006.01)
 *A61B 5/0205* (2006.01)
 (Continued)

(52) U.S. Cl.
 CPC ........ *A61B 5/02055* (2013.01); *A61B 5/6824* (2013.01); *A61B 5/021* (2013.01);
 (Continued)

(58) Field of Classification Search
 CPC ... A61B 5/0205; A61B 5/02055; A61B 5/021; A61B 5/02108; A61B 5/02116;
 (Continued)

(56) References Cited

U.S. PATENT DOCUMENTS

| 5,079,535 A | 1/1992 | Neuman |
| 6,647,287 B1 * | 11/2003 | Peel, III ............. A61B 5/02125 600/485 |

(Continued)

FOREIGN PATENT DOCUMENTS

| CN | 103219066 A | 7/2013 |
| WO | WO 2014/066802 A1 | 5/2014 |
| WO | WO 2015/179320 A1 | 11/2015 |

OTHER PUBLICATIONS

Alberto Avolio, "Central Aortic Blood Pressure and Management of Hypertension," Hypertension, pp. 1005-1007, December (Year: 2013).*

(Continued)

*Primary Examiner* — Ahmed M Farah
(74) *Attorney, Agent, or Firm* — Knobbe, Martens, Olson & Bear, LLP

(57) ABSTRACT

An apparatus comprising a wearable device comprising a supporting structure, a sensor and an electronics module, wherein the supporting structure is configured to press the sensor against a skin surface of a subject, wherein the sensor is configured to detect a biological metric of the subject, and wherein the electronics module is configured to quantify and/or transmit one or more signal(s) corresponding to the biological metric. Some aspects relate to a method of monitoring a biological metric in a subject comprising: adorning a subject with the wearable device; and detecting the biological metric over a period of time in the subject with the wearable device. Other aspects relate to a method of treating a disease in a subject comprising: monitoring a biological metric in the subject over a period of time, and treating the subject with a therapeutic protocol, and monitoring the biological metric in the subject to assess treatment efficacy. Method are provided for estimating a central aortic pressure waveform in a subject comprising: measuring a (Continued)

radial artery pressure waveform in the subject and transforming the radial artery pressure waveform to a central aortic pressure waveform using a transfer function.

7 Claims, 18 Drawing Sheets

(51) Int. Cl.
  *A61B 5/00*     (2006.01)
  *A61B 5/024*    (2006.01)
  *A61B 5/08*     (2006.01)
  *A61B 5/145*    (2006.01)

(52) U.S. Cl.
  CPC ............ *A61B 5/024* (2013.01); *A61B 5/0816* (2013.01); *A61B 5/14542* (2013.01); *A61B 2562/0247* (2013.01); *A61B 2562/0261* (2013.01); *A61B 2562/0285* (2013.01); *A61B 2562/12* (2013.01)

(58) Field of Classification Search
  CPC . A61B 5/02125; A61B 5/022; A61B 5/05508; A61B 5/02225; A61B 5/02233; A61B 5/02241; A61B 2562/00; A61B 2562/0247
  USPC ................ 600/301, 480, 481, 485, 490–494, 600/500–503
  See application file for complete search history.

(56) References Cited

U.S. PATENT DOCUMENTS

| | | | |
|---|---|---|---|
| 9,538,924 B1* | 1/2017 | Asiri | B82Y 5/00 |
| 10,405,806 B2* | 9/2019 | Baik | A61B 5/7278 |
| 2002/0038090 A1* | 3/2002 | Sunagawa | A61B 5/02116 600/485 |
| 2002/0130673 A1 | 9/2002 | Pelrine et al. | |
| 2005/0080349 A1 | 4/2005 | Okada et al. | |
| 2006/0169989 A1 | 8/2006 | Bhattacharya et al. | |
| 2006/0283262 A1 | 12/2006 | Smits et al. | |
| 2008/0001735 A1* | 1/2008 | Tran | G06F 19/3418 340/539.22 |
| 2008/0119896 A1 | 5/2008 | Wong et al. | |
| 2011/0137577 A1 | 6/2011 | Chen | |
| 2011/0253288 A1 | 10/2011 | Xie | |
| 2011/0278040 A1 | 11/2011 | Zhang et al. | |
| 2012/0035508 A1 | 2/2012 | Van Leer | |
| 2012/0086433 A1 | 4/2012 | Cheng et al. | |
| 2012/0121870 A1 | 5/2012 | Toury et al. | |
| 2012/0176237 A1* | 7/2012 | Tabe | F41H 3/02 340/539.12 |
| 2013/0102909 A1* | 4/2013 | Mukkamala | A61B 5/7246 600/485 |
| 2013/0140611 A1 | 6/2013 | Kim et al. | |
| 2013/0264912 A1 | 10/2013 | Kwon et al. | |
| 2013/0281861 A1* | 10/2013 | Flomerfelt | A61B 8/02 600/454 |
| 2013/0312541 A1 | 11/2013 | Majidi et al. | |
| 2014/0054599 A1 | 2/2014 | Choi et al. | |
| 2014/0290376 A1 | 10/2014 | Rahajandraibe | |
| 2015/0034237 A1 | 2/2015 | Biggs et al. | |
| 2015/0263235 A1 | 9/2015 | Shin et al. | |
| 2015/0294805 A1 | 10/2015 | Hayward et al. | |
| 2016/0302678 A1* | 10/2016 | Stok | A61B 5/02125 |
| 2017/0219331 A1* | 8/2017 | Pegan | G01L 1/2287 |
| 2018/0228380 A1* | 8/2018 | Qasem | A61B 5/0225 |

OTHER PUBLICATIONS

Bandodkar, A.J., and Wang, J. 2014. "Non-invasive wearable electrochemical sensors: a review" *Trends Biotechnol* 32: 363-371.

Biagiotti, V. et al. 2012 "Probe accessibility effects on the performance of electrochemical biosensors employing DNA monolayers" *Anal. Bioanal. Chem.* 402: 413-421.

Drelich, J. and Chibowski, E. 2010 "Superhydrophilic and superwetting surfaces: Definition and mechanisms of control" *Langmuir* 26: 18621-18623.

Freschauf, L.R. et al. 2012 "Shrink-induced superhydrophobic and antibacterial surfaces in consumer plastics" *PLoS One* 7: e40987 (in 7 pages).

Fu et al. 2009 "Tunable nanowrinkles on shape memory polymer sheets" *Adv Mater* 21: 4472-4476.

Gabardo, C. et al. 2013 "Bench-top fabrication of hierarchically structured high surface-area electrodes" *Adv. Funct. Mater.* 23: 3030-3039.

Gabardo, C.M. et al. 2015 "Rapid prototyping of microfluidic devices with integrated wrinkled gold micro-/nano textured electrodes for electrochemical analysis" *Analyst* 140: 5781-5788.

Hauke et al. 2017 "Superwetting and aptamer functionalized shrink-induced high surface area electrochemical sensors" *Biosensors and Bioelectronics* 94: 438-442.

Heikenfeld, J., 2016 "Non-invasive analyte access and sensing through eccrine sweat: challenges and outlook circa 2016" *Electroanalysis* 28: 1242-1249.

Kimmel, D.W. et al. 2012 "Electrochemical sensors and biosensors" *Anal. Chem.* 84: 685-707.

Lubin, A.A. and Plaxco, K.P., 2010 "Folding-based electrochemical biosensors: the case for responsive nucleic acid architectures" *Acc. Chem. Res.* 43: 496-505.

Pegan, J.D. et al. 2013 "Flexible shrink-induced high surface area electrodes for electrochemiluminescent sensing" *Lab Chip* 13: 4205-4209.

Pheeny, C.G. and Barton, J.K. 2012 "DNA electrochemistry with tethered methylene blue" *Langmuir* 28: 7063-7070.

Rowe, A.A. et al. 2010 "Reagentless measurement of aminoglycoside antibiotics in blood serum via an electrochemical, ribonucleic acid aptamer-based biosensor" *Anal. Chem.* 82: 7090-7095.

Salvarezza, R.C. et al. 1990 "Monte Carlo simulation applicable to the growth of rough metal overlayers: parametric relationships related to the electrochemical roughening" *Phys. Rev. B* 41: 502-512.

Setia, U. and Gross, P.A. 1976 "Administration of tobramycin and gentamicin by the intravenous route every 6 h in patients with normal renal function" *J. Infect. Dis.* 134: S125-129.

Sonney, S. et al. 2015 "Rapid bench-top fabrication of poly(dimethylsiloxane), polystyrene microfluidic devices incorporating high-surface area sensing electrodes" *Biomicrofluidics* 9: 026501 (in 11 pages).

Ausman et al. 2000 "Organic Solvent Dispersions of Single-Walled Carbon Nanotubes: Toward Solutions of Pristine Nanotubes" *J Phys Chem B* 104: 8911-8915.

Byun I. et al. 2013 "Transfer of thin Au films to polydimethylsiloxane (PDMS) with reliable bonding using (3-mercaptopropyl)trimethoxysilane (MPTMS) as a molecular adhesive" *J Micromech Microeng* 23(8): 1-10.

Chen et al. 1997 "Estimation of central aortic pressure waveform by mathematical transformation of radial tonometry pressure" *Circulation* 95:1827-1836.

Chirinos, J. A. et al. 2011 "Ethnic differences in arterial wave reflections and normative equations for augmentation index" *Hypertension* 57: 1108-1116.

Dumonteil et al. 2006 "Dispersion of carbon nanotubes using organic solvents" *J Nanosci Nanotechnol* 6(5): 1315-1318.

Kohara, K. et al. 2005 "Radial augmentation index: A useful and easily obtainable parameter for vascular aging" *Am J Hypertens* 18: 14-17.

Li et al. 2012 "Dispersion of Carbon Nanotubes in Organic Solvents Initiated by Hydrogen Bonding Interactions" *AIChE Journal* 58: 2997-3002.

Lipomi et al. 2011 "Skin-like pressure and strain sensors based on transparent elastic films of carbon nanotubes" *Nature Nanotechnology* 6: 788-792.

(56) References Cited

OTHER PUBLICATIONS

Nelson et al., 2010 "Noninvasive Measurement of Central Vascular Pressures With Arterial Tonometry: Clinical Revival of the Pulse Pressure Waveform?" *Mayo Clin Proc* 85(5): 460-472.

Schwartz et al. (2013 "Flexible polymer transistors with high pressure sensitivity for application in electronic skin and health monitoring" *Nature Communications* 4: 1859 (in 8 pages).

Wang et al. 2014 "Silk-Molded Flexible, Ultrasensitive, and Highly Stable Electronic Skin for Monitoring Human Physiological Signals" *Advanced Materials* 26: 1336-1342.

\* cited by examiner

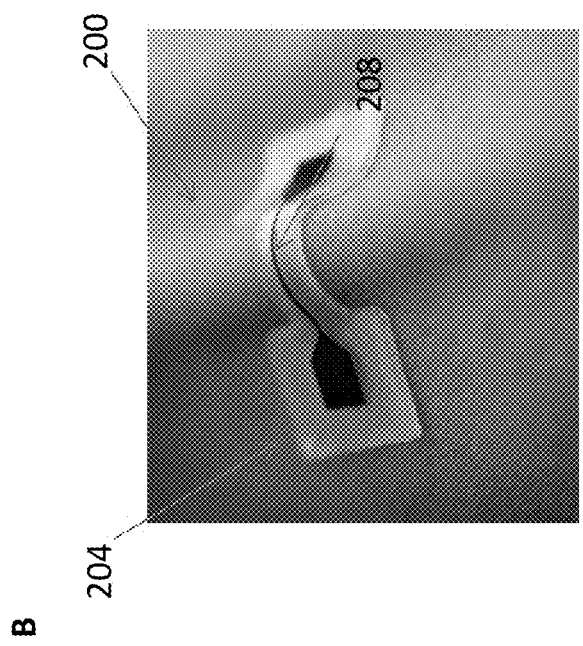
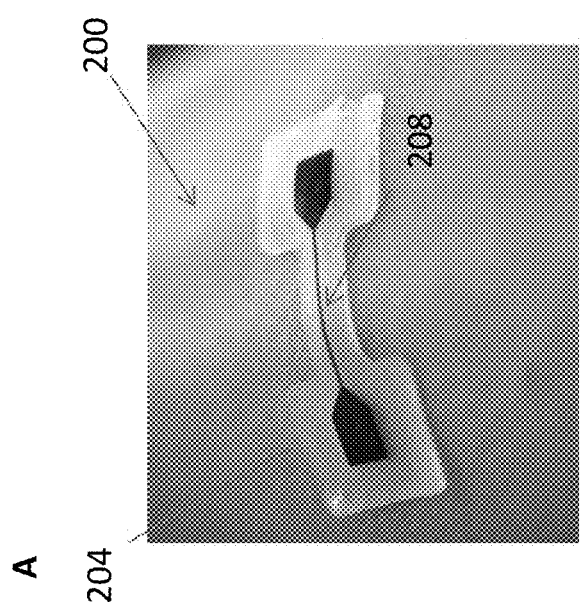
Fig. 9

VITAL SIGNS MONITOR

STATEMENT REGARDING FEDERALLY SPONSORED R&D

This invention was made with government support under funds awarded by the National Science Foundation DGE-1321846. The government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This application is directed to monitor devices for tracking patient vital signs, such as blood pressure, in a convenient low cost manner.

Description of the Related Art

Measuring a patient's vital signs is routine clinical protocol. In a hospital setting, measuring multiple vital signs requires multiple, large and bulky devices. Clinicians are required to operate these devices and hand record measurements, which takes up valuable clinician time.

Current vital signs monitoring devices are largely outdated. The blood pressure cuff device, for example, uses the same sphygmomanometer technology that has been used for over a century. Low cost blood pressure cuffs are manually operated and can only take periodic measurements. There is a need for automatic, continuous vital signs monitoring. Currently no wireless devices exist for taking numerous, clinically relevant vitals measurements at once. Most devices are specific to measuring only one vital sign, such as a blood pressure, heart rate, blood oxygenation, and temperature.

SUMMARY OF THE INVENTION

A vitals band is a device that can be deployed around a portion of a patient to measure vital signs. For example a vitals band can be implemented as a wristband that can be easily applied to a patient's wrist and continuously monitor various vital signs. The band incorporates one or a plurality of sensors that obtain clinically relevant vitals data, including blood pressure, heart rate, blood oxygen and temperature. A vitals band can also incorporate a wireless communication protocol, such as near field communication, Bluetooth, etc. to wirelessly communicate data, for example to a doctor's smart mobile device.

Some embodiments relate to an apparatus comprising a wearable device comprising a supporting structure, a sensor and an electronics module, wherein the supporting structure is configured to press the sensor against a skin surface of a subject, wherein the sensor is configured to detect a biological metric of the subject, and wherein the electronics module is configured to quantify and/or transmit one or more signal(s) corresponding to the biological metric.

In some embodiments, the apparatus further comprises a user system that is configured to receive and display the one or more signal(s) transmitted by the electronics module.

Some embodiments relate to a method of monitoring blood pulse rate and/or blood pressure in a subject comprising: adorning a subject with the wearable device; and detecting blood pulse rate and/or blood pressure in the subject with the wearable device.

In some embodiments, the sensor comprises a thin film metal strain gauge.

In some embodiments, the sensor comprises a one-dimensional structure.

In some embodiments, the one-dimensional structure is selected from the group consisting of a nanotube and a nanowire.

In some embodiments, the sensor comprises a planar film sensor.

In some embodiments, the sensor comprises two sensing modalities in a face-to-face configuration.

In some embodiments, the supporting structure comprises a flexible, bistable spring band that is configured to wrap around and secure the apparatus to a wearer.

In some embodiments, the electronics module is comprised within a housing disposed on an inner or an outer side of the supporting structure.

In some embodiments, the electronics module is contained within the supporting structure.

In some embodiments, the apparatus further comprises a user system that is configured to receive and display the one or more signal(s) transmitted by the electronics module.

In some embodiments, the user system is configured to wirelessly receive the one or more signal(s) transmitted by the electronics module.

In some embodiments, the electronics module comprises one or more components selected from the group consisting of a processor, a memory, a battery, and a radio circuit configured to transmit data to an external system.

In some embodiments, the user system is configured to display static and/or continuous blood pulse rate and/or blood pressure measurements.

Some embodiments relate to a method of monitoring a biological metric in a subject comprising: (1) adorning a subject with a wearable device as disclosed herein; and (2) detecting the biological metric over a period of time in the subject with the wearable device.

In some embodiments, the wearable device is worn on a wrist of the subject.

In some embodiments, the biological metric is selected from the group consisting of a heartbeat rate, a blood pressure, blood oxygenation, respiration rate and temperature.

Some embodiments relate to a method of treating a disease in a subject comprising: (1) monitoring a biological metric in the subject according to any technique disclosed herein over a period of time, (2) treating the subject with a therapeutic protocol, and (3) monitoring the biological metric in the subject to assess treatment efficacy.

Some embodiments relate to a method of estimating a central aortic pressure waveform in a subject comprising: (1) measuring a radial artery pressure waveform in the subject by using an apparatus as disclosed herein, and (2) transforming the radial artery pressure waveform to a central aortic pressure waveform using a transfer function.

In some embodiments, the transfer function describes the properties of a system on the basis of its immediate past input and output data.

In some embodiments, the transfer function uses the relation:

$$T(t) = -a_1 T(t-1) - a_2 T(t-2) - \ldots - a_{na} T(t-na) + b_1 P(t-1) + \ldots + b_{nb} P(t-nb) \quad (1)$$

where T(t) and T(t−I) [I=1, 2 . . . na] are present and previous output (radial tonometer) discrete measurements, respectively, and P(t−I) are previous input (aortic pressure) discrete measurements, $a_1$, $a_2$, $a_{na}$ and $b_{nb}$ are parameters of the model, and na and nb represent a number of previous input-output values used to describe the present output.

BRIEF DESCRIPTION OF THE DRAWINGS

FIG. 9 (A and B) show conformability of an embodiment of a sensor apparatus according to the methods herein.

DETAILED DESCRIPTION OF THE PREFERRED EMBODIMENT

Disclosed herein are systems, methods and apparatuses for monitoring vital signs of a subject Vital signs are measurements of the body's most basic functions. The four main vital signs routinely monitored by medical professionals and health care providers include body temperature, pulse rate, respiration rate (rate of breathing) and blood pressure. The system can include a strain sensor configured to measure pulse rate, respiration rate and blood pressure. The state of health of a subject can be inferred by quantifying vital signs. By continuously monitoring vital signs, changes in the health of the subject can be sensed and the subject can be prompted to go to the hospital for medical supervision or urgent care. Importantly, the systems, methods, and apparatuses can measure vital signs noninvasively.

Figure 1:
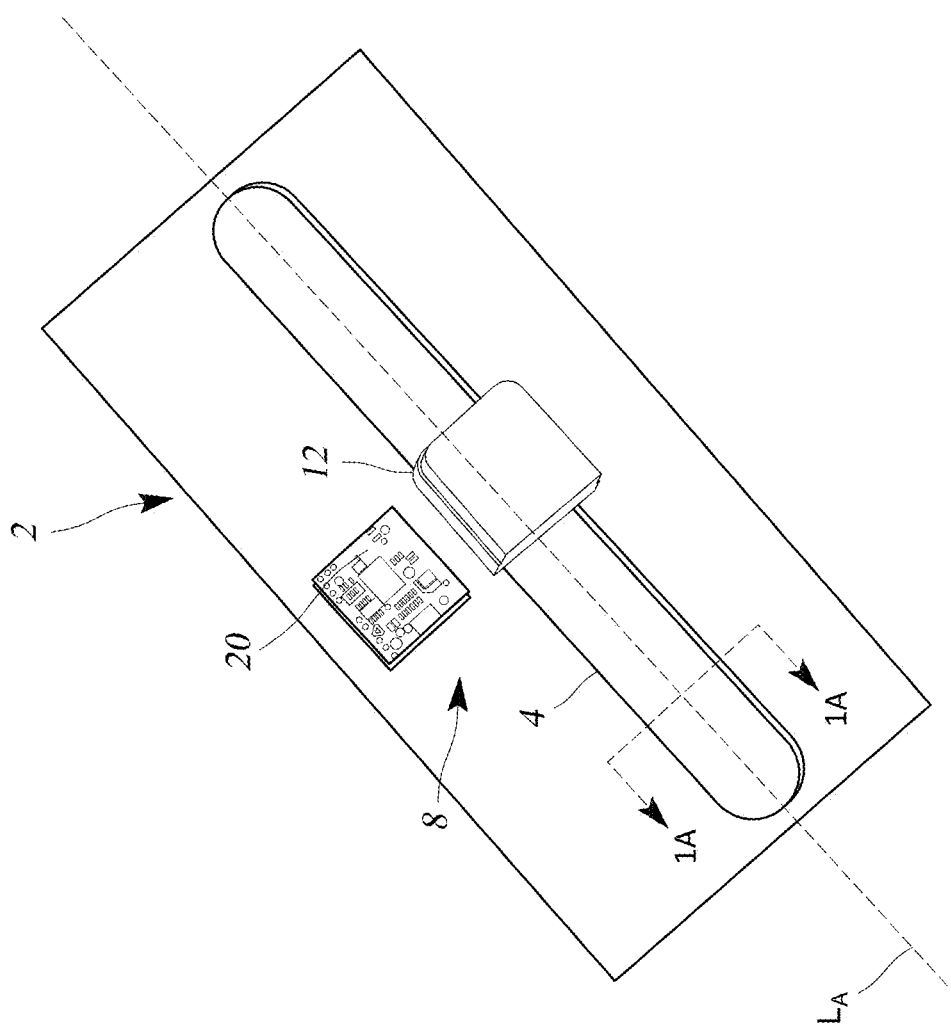
FIG. 1 is a perspective view of a vitals band according to one embodiment of this application.
Figure 2:
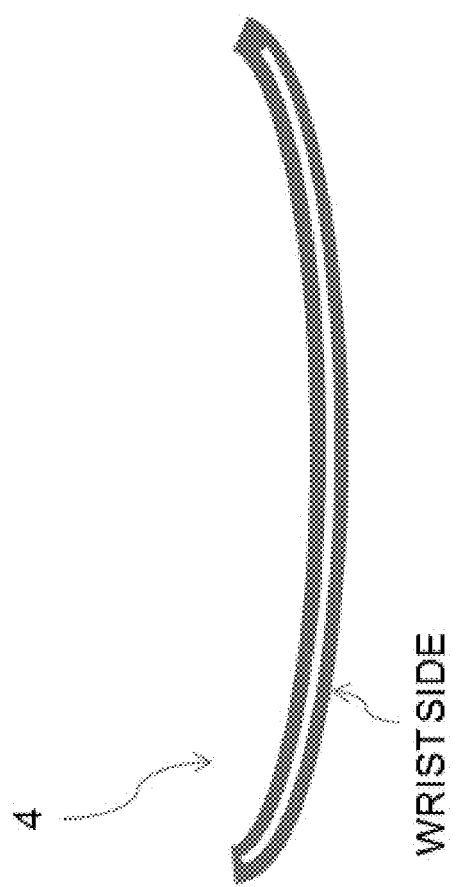
FIG. 2 depicts a transverse cross-section at the plane 1A-1A defined in FIG. 1.
Figure 3:
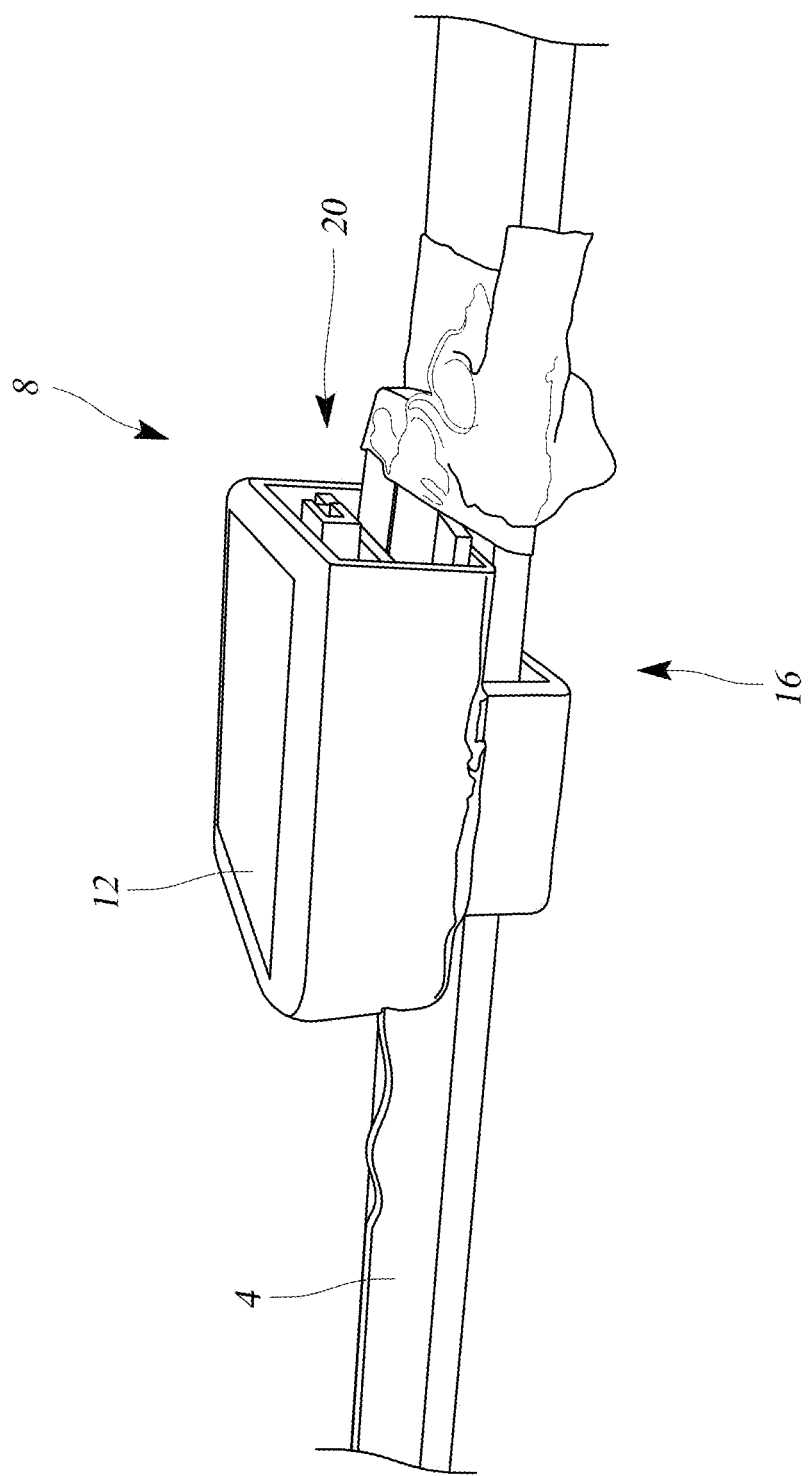
FIG. 3 is a system diagram comprising components of a vitals band according to one embodiment.
Figure 4:
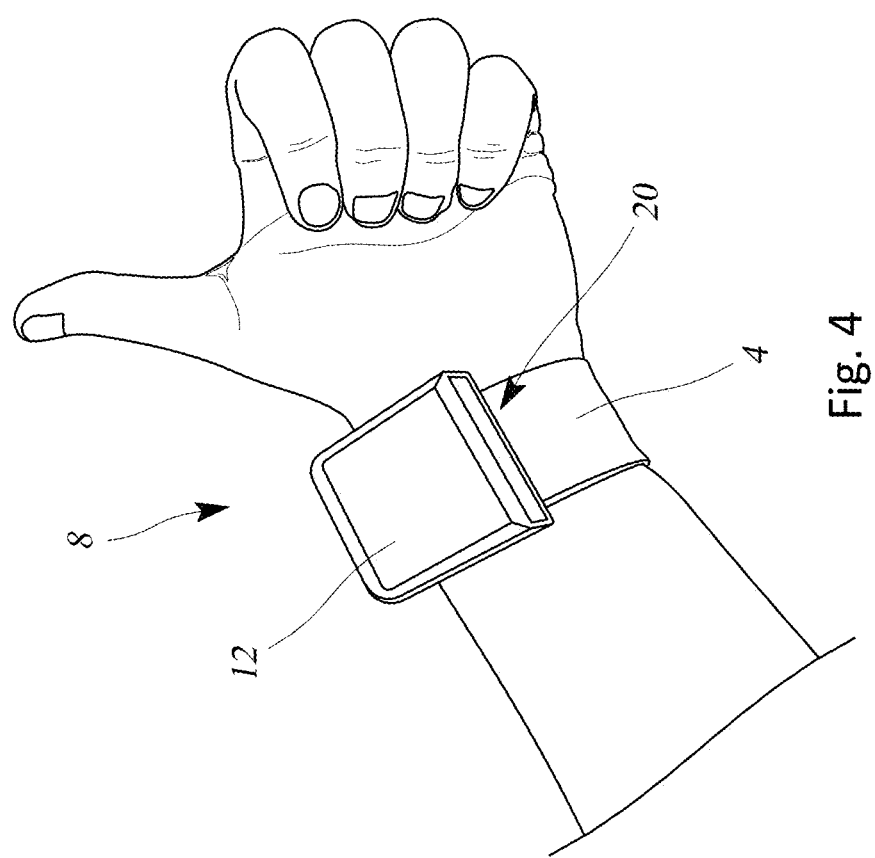
FIG. 4 depicts one embodiment of the vitals band being worn by a subject.
Figure 5:
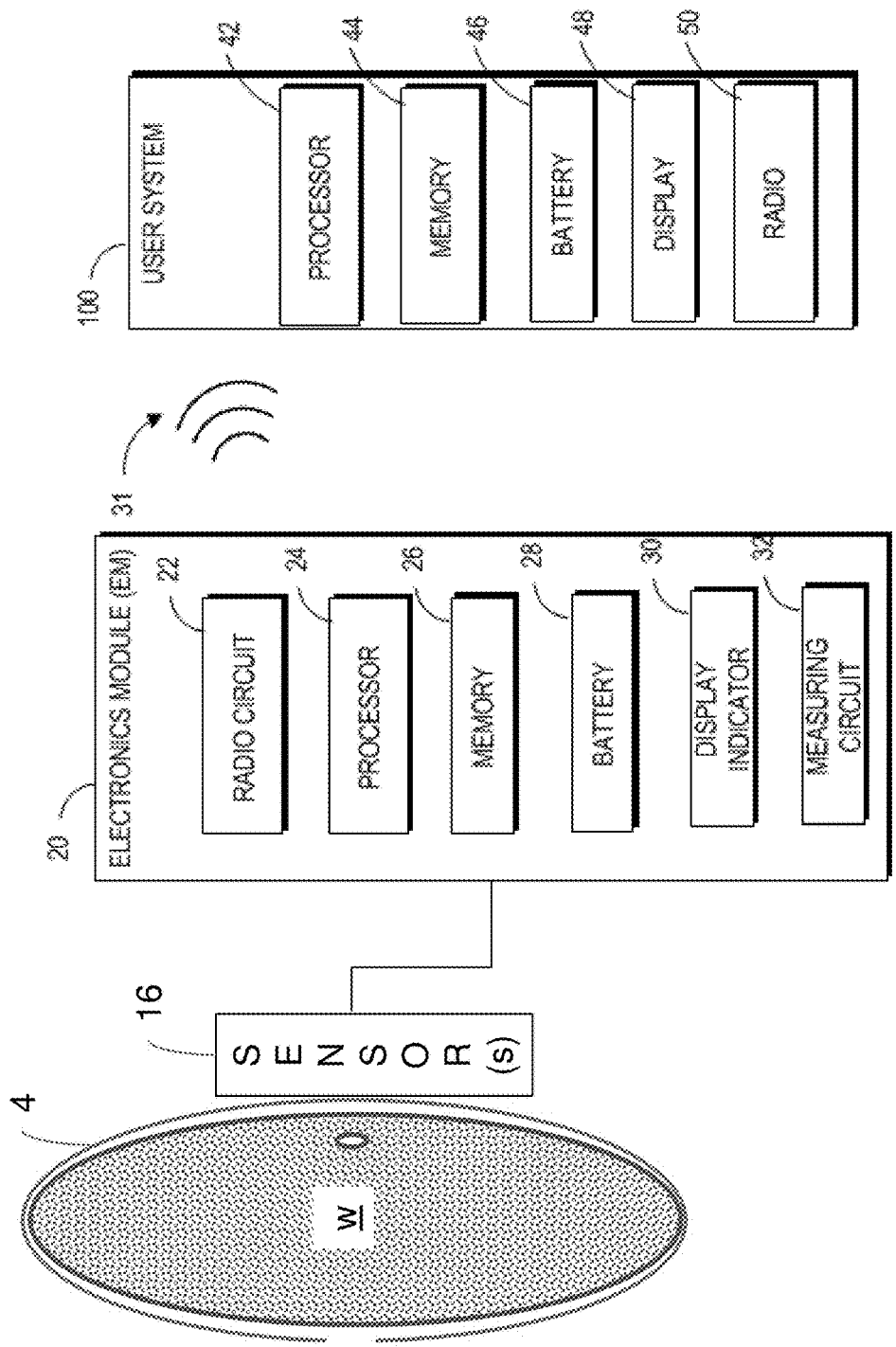
FIG. 5 shows a wearable sensor, an electronics module (EM) and a user system.

In one embodiment a vitals band 2 is implemented as a self-supporting band 4 that can be placed in a flat configuration, as shown in FIG. 1, and can be self-supporting on the patient as shown in FIG. 4. The self-supporting band 4 can be quickly applied to a patient or user by wrapping around a wrist W or other portion of an extremity. In some embodiments, a slap band design can be provided. The slap band naturally lies flat, but when "slapped" against a surface, such as the wrist, the band bends inward, rolling up around the wrist. A slap band includes a flexible, bistable, spring band, e.g., a stainless steel band, sealed within a fabric, silicone, or polymer cover. The band can be straightened out, making tension within the spring band. The straightened band is then slapped against a curved object, e.g., a wearer's forearm, causing the band to spring back into a curve that wraps around the forearm, securing the band to the wearer. The band itself can be a concave strip of metal or other resilient material, covered with a polymer or silicone. The concavity can be disposed in a direction transverse to the longitudinal axis $L_A$ of the band 4.

Vitals measurements occur through a sensor assembly 8 including a housing 12 and one or more sensors 16 incorporated into the housing 12. The housing 12 can be disposed on an inner or an outer side of, the slap band. In some cases, there is not a separate housing but the band 4 directly houses the sensor(s) 16. The slap band has a capability to monitor blood pressure in one embodiment Cuff-less blood pressure measurement at the wrist is not common because highly sensitive pressure sensors are required to detect the low pressures produced by the radial artery at the wrist Schwartz et al. (2013 "Flexible polymer transistors with high pressure sensitivity for application in electronic skin and health monitoring" *Nature Communications* 4: 1859) demonstrated that flexible polymer thin film sensors were capable of measuring pulse wave at the radial artery. Pulse wave can be used to determine peripheral blood pressure and an FDA-approved algorithm can then derive central blood pressure indices (Nelson et al., 2010 "Noninvasive Measurement of Central Vascular Pressures With Arterial Tonometry: Clinical Revival of the Pulse Pressure Waveform?" *Mayo Clin Proc* 85(5): 460-472). Nelson and Schwartz are hereby incorporated by reference herein. Our laboratory develops flexible polymer thin film sensors. These sensors include wrinkled surface effects that are much higher than the average roughness of commercial shrink film, as discussed below.

In one embodiment, the sensor 16 for the vitals band can be formed by a process in which a carbon nanotube (CNT) solution is sprayed on polystyrene (PS). The structure including the CNT and the PS is then shrunk at elevated temperature. The stiffness mismatch between the CNT layer and the PS creates wrinkles in the CNT film, increasing its conductivity. The wrinkled CNT film can then be transferred to polydimethylsiloxane (PDMS), a soft polymer. Increased sensitivity can be provided by selecting an appropriate CNT thickness and polymer thickness, such that low pressure at the radial artery can be sensed and accurately measured. Further details of CNT methods are discussed below in connection with FIGS. 3-6

The vitals band 2 can also include electronics module 20 that receives and process a signal from the sensor 16. The electronics module 20 can include a processor 24, memory 26 (e.g., flash memory), a battery 28, and a radio circuit 22 for transmitting data to an external user system 100 over a link 31. The radio circuit 22 can be implemented as any form of wireless communications, e.g., near field communications, Bluetooth, or other protocol. The electronics module 20 can be disposed in the housing 12 or directly into the band 4. Further details of the electronics module 20 and the eternal user system 100 are discussed below.

In one embodiment of the vitals band, the sensor(s) 16 and band 4 can be produced in a low cost manner and in disposable form and at least some of the electronics, e.g., the electronics module 20 can be configured for re-use. For example, re-usable electronics module 20 can be disposed in the housing 12 and snapped into a new self-supporting band 4 for reuse. Each band 4 can have one or more sensor(s) 16 disposed therein, which sensors can be disposable.

Pulse Rate

Pulse rate is a measurement of heart rate, or the number of times the heart beats per minute. As the heart pushes blood through the arteries, the arteries expand and contract with the flow of the blood. Taking a pulse not only measures the heart rate, but also can indicate Heart rhythm and strength of the pulse. The normal pulse for healthy adults ranges from 60 to 100 beats per minute. The pulse rate may fluctuate and increase with exercise, illness, injury, and emotions. Females ages 12 and older, in general, tend to have faster heart rates than do males. Athletes, such as runners, who do a lot of cardiovascular conditioning, may have heart rates near 40 beats per minute and experience no problems.

Respiration Rate

Respiration rate is the number of breaths a person takes per minute. The rate is usually measured when a person is at rest and simply involves counting the number of breaths for one minute by counting how many times the chest rises. Respiration rates may increase with fever, illness, and with other medical conditions. When checking respiration, it is important to also note whether a person has any difficulty breathing. Normal respiration rates for an adult person at rest range from 12 to 16 breaths per minute.

Blood Pressure

Blood pressure is the force of the blood pushing against the artery walls. Each time the heart beats, it pumps blood into the arteries, resulting in the highest blood pressure as the heart contracts.

Two numbers are recorded when measuring blood pressure. The higher number, or systolic pressure, refers to the pressure inside the artery when the heart contracts and pumps blood through the body. The lower number, or diastolic pressure, refers to the pressure inside the artery when the heart is at rest and is filling with blood. Both the systolic and diastolic pressures are traditionally recorded as "mm Hg" (millimeters of mercury). This recording represents how high the mercury column in an old-fashioned manual blood pressure device (called a mercury manometer) is raised by the pressure of the blood.

High blood pressure, or hypertension, directly increases the risk of coronary heart disease (heart attack) and stroke (brain attack). With high blood pressure, the arteries may have an increased resistance against the flow of blood, causing the heart to pump harder to circulate the blood.

According to the National Heart, Lung, and Blood Institute (NHLBI) of the National Institutes of Health, high blood pressure for adults is defined as 140 mm Hg or greater systolic pressure or 90 mm Hg or greater diastolic pressure. In an update of NHLBI guidelines for hypertension in 2003, a new blood pressure category was added called prehypertension: 120 mm Hg-139 mm Hg systolic pressure or 80 mm Hg-89 mm Hg diastolic pressure. The NHLBI guidelines now define normal blood pressure as follows: Less than 120 mm Hg systolic pressure and Less than 80 mm Hg diastolic pressure.

Noninvasive Measurement of Central Vascular Pressures with Arterial Tonometry

With current sphygmomanometric and oscillometric devices, only the peak and trough of the peripheral arterial pulse waveform are clinically used. Several limitations exist with peripheral blood pressure. First, central aortic pressure is a better predictor of cardiovascular outcome than peripheral pressure. Second, peripherally obtained blood pressure does not accurately reflect central pressure because of pressure amplification. Lastly, antihypertensive medications have differing effects on central pressures despite similar reductions in brachial blood pressure. Applanation tonometry (AT), which is a noninvasive, reproducible, and accurate representation of the aortic pressure waveform, can overcome the limitations of peripheral pressure by determining the shape of the aortic waveform from the radial artery. Waveform analysis not only indicates central systolic and diastolic pressure but also determines the influence of pulse wave reflection on the central pressure waveform. It can serve as a useful adjunct to brachial blood pressure measurements in initiating and monitoring hypertensive treatment, in observing the hemodynamic effects of atherosclerotic risk factors, and in predicting cardiovascular outcomes and events. Radial artery applanation tonometry is a noninvasive, reproducible, and affordable technology that can be used in conjunction with peripherally obtained blood pressure to guide patient management.

Radial Artery Applanation Tonometry

The limitations of peripheral blood pressure measurements may be overcome with AT. Tonometry of the radial artery provides an accurate, reproducible, noninvasive assessment of the central pulse pressure (PP) waveform. Tonometry means "measuring of pressure," whereas applanation means "to flatten." Radial artery AT is performed by placing a hand-held tonometer (strain gauge pressure sensor)

over the radial artery and applying mild pressure to partially flatten the artery (FIG. 4). The radial artery pressure is then transmitted from the vessel to the sensor (strain gauge) and is recorded digitally. A mathematical formula using a fast Fourier transformation has resulted in a Food and Drug Administration-approved algorithm that permits derivation and calculation of central pressure indices from a peripheral brachial blood pressure and concomitant recording of a PP wave with radial tonometry. Transfer functions are accurate in predicting central pressures. Measurements of central pressures with AT are easily reproducible even in the hands of novices. Radial artery AT, as opposed to carotid artery evaluation, is more comfortable for the patient and is easier to use in the clinical setting.

Clinical Utility of Radial Arterial Tonometry

Radial artery AT may be more predictive of clinical cardiovascular events than peripheral cuff pressures and provide a valuable addition to determination of brachial blood pressure in the management of hypertension.

Sleep-disordered breathing, the most common form of which is obstructive sleep apnea (OSA), is an important entity in resistant hypertension. Obstructive sleep apnea may exert its detrimental effects by perturbations of central pressures well before peripheral increases in blood pressure or other related cardiovascular phenomena such as arrhythmias become apparent to clinicians. Radial artery AT could hence be valuable as a measure of response to therapy in patients with OSA.

Excess left ventricle (LV) mass is a result of LV loading and indicates end organ effects of elevated blood pressure. Measuring augmentation pressure (AP), augmentation index (Aix), and pulse amplification in response to blood pressure therapy may assist a clinician in following up patients who are experiencing regression of left ventricle (LV) mass under therapy.

Radial artery AT may alert a clinician to those at risk of diastolic dysfunction (DD).

The central pressure waveform may indicate the presence and severity of coronary artery disease (CAD). Tobacco smoking is a well-known risk factor for the development of CAD. The central pressure waveform may also identify a population at risk of peripheral vascular disease.

In diabetic patients, radial artery AT may indicate changes in measurements of central pressure before measurements of peripheral blood pressure. Certainly, early recognition of unfavorable central vascular changes in patients with diabetes may lead to the timely addition of vasodilators to the patient's treatment regimen before changes in brachial pressure are noted.

Hyperlipidemia (HLD) may lead to augmented central systolic blood pressure (SBP).

Flexible Miniaturized Sensor Apparatuses

FIGS. 6-14 illustrate a variety of structures that can be incorporated into the sensor apparatus 100 to reliably detect a fluctuating signal, such as a detectable change in resistance, for motion detection in a disposable wearable sensor. FIGS. 6-9 illustrate thin film metal strain gauges, FIGS. 10-14 illustrate one-dimensional structures, including nanotubes and nanowires for use as disposable wearable strain gauge sensors.

Sensors Having a Metal Film Conductor

Figure 6:
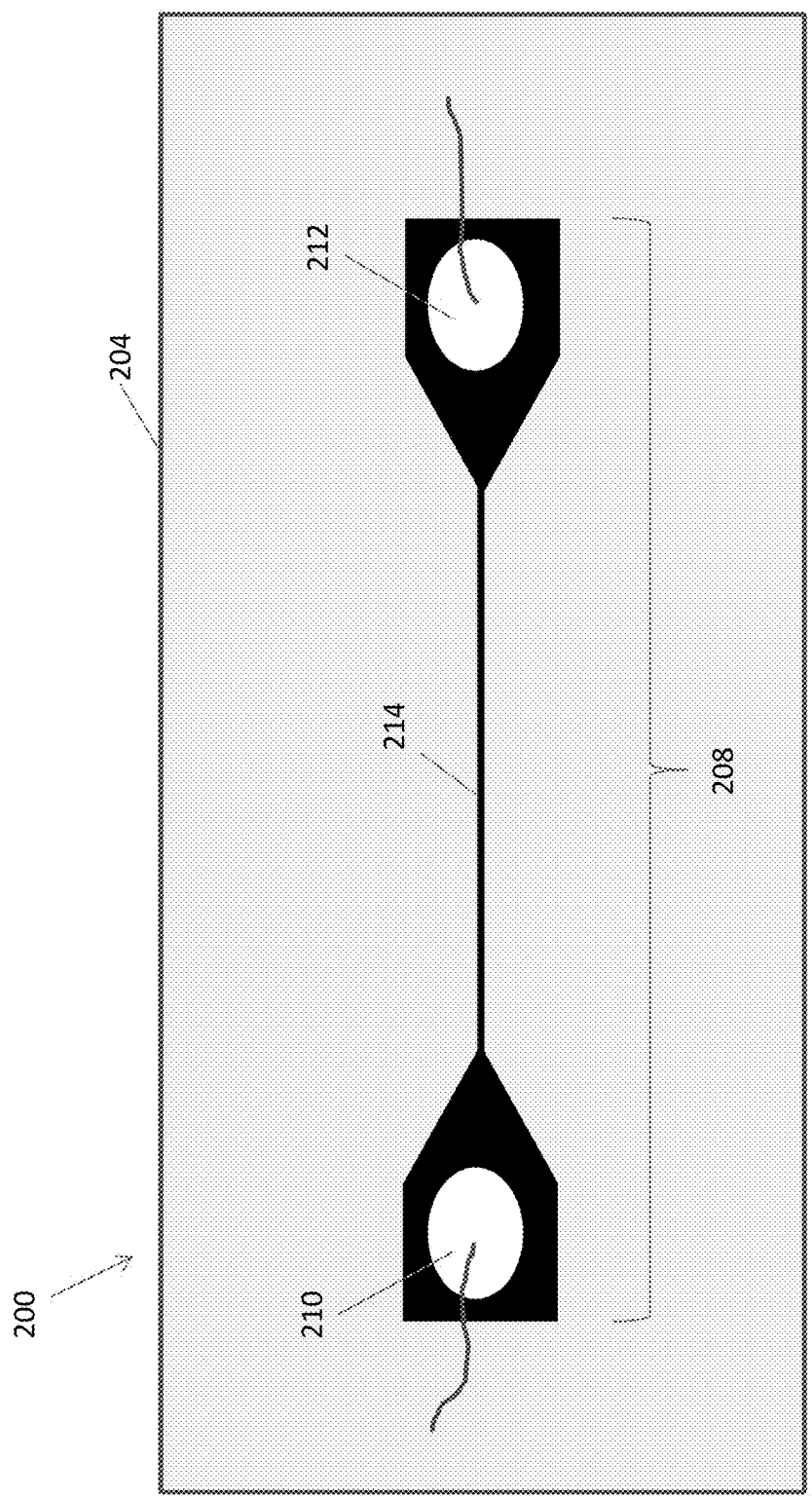
FIG. 6 depicts an embodiment of a sensor, including a wrinkled metal film strain gauge.
Figure 7:
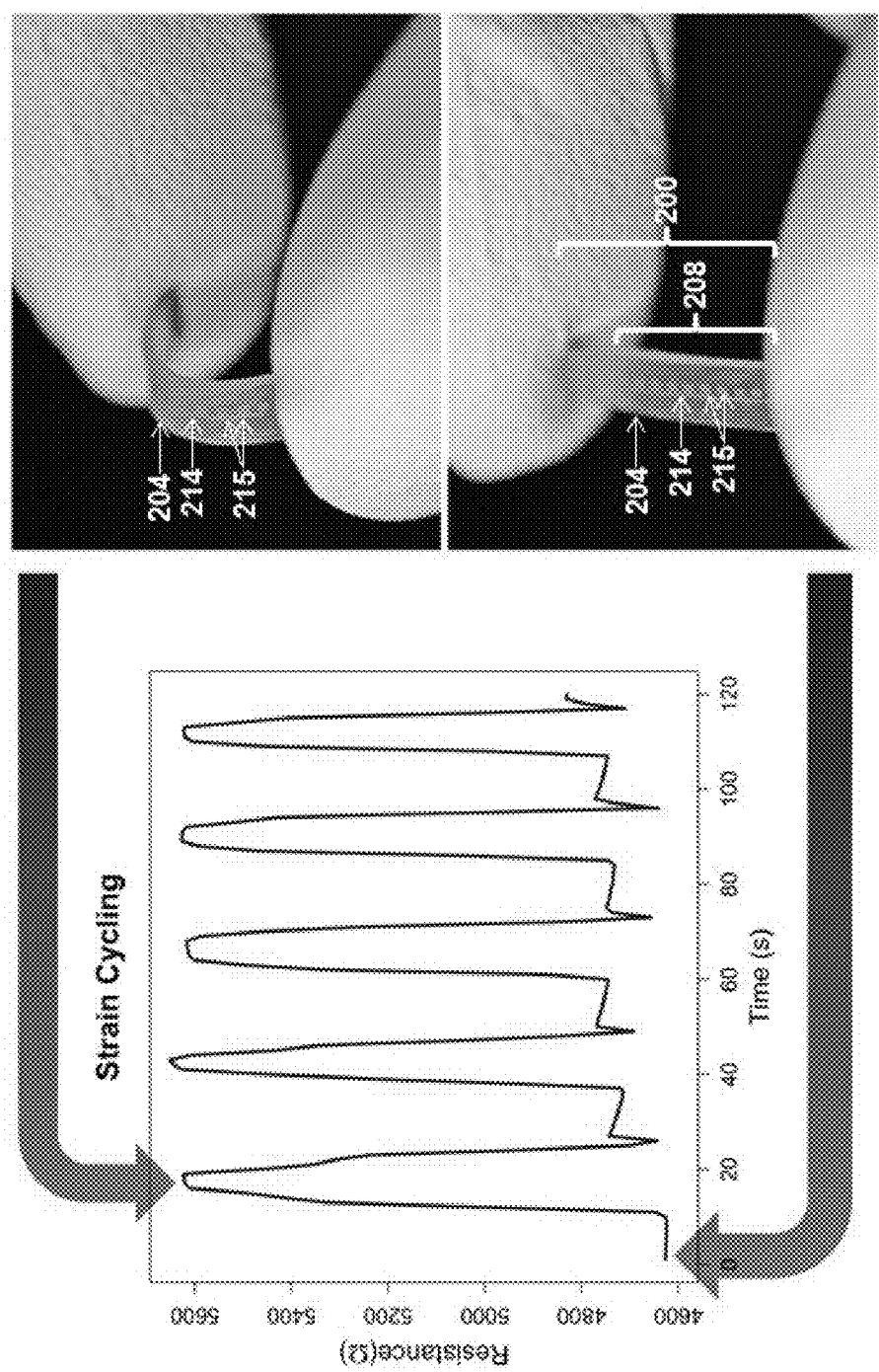
FIG. 7 shows the resistance response of a wrinkled metal film strain gauge. Resistance peaks correspond with maximum strain of 5%. The bottom arrow indicates the initial, unstrained resistance of the wrinkled metal film strain gauge.

In one embodiment, as depicted in FIG. 6, the sensor apparatus 200 includes a flexible substrate 204 and a conductor 208. In the illustrated embodiment, the conductor 208 initially is formed as a thin metal film but thereafter crumpled or wrinkled because the material it is formed upon is shrunk to a fraction of its initial size. A plurality of electrical contacts 210 and 212 are in electrical communication with the conductor 208. The electrical contacts 210, 212 can be disposed at opposite ends of an elongate conductive region 214. In other embodiment, more than two contacts can be provided. For example, FIG. 7 shows one modified embodiment in which a plurality of contacts 215 are disposed along the length of an elongate conductive region 214 on flexible substrate 204. The contacts 215 in this embodiment are disposed to one side of the elongate conductive region and allow connection to other devices at a number of different positions and/or permit a number of different devices to be in contact with the elongate conductive region. For example, any two of the contacts 215 can be used to measure a signal such as current or a change in a property such as resistance at a location along the conductive region 214.

The sensor apparatus 200 is able to undergo very high strain, which induces a detectable change in a signal as illustrated in FIG. 7. The signal can be a change in resistance.

One configuration that enables high range of strain is the physical configuration of the film conductor 208. In particular, at the micron-scale the conductor 208 is not flat but rather is crumpled or wrinkled. This configuration can exhibit secondary folding in some embodiments. Non-shrunk and shrunk electrodes have a linear decrease in resistance across patterned line electrodes of different widths. Measuring electrical resistivity before and after the thermal shrinking process shows a dramatic improvement in electrical conductivity of wrinkled Au thin film electrodes over the non-shrunk, planar Au electrodes. Cross-sections of the wrinkled metal films reveal many tens of micron-scale invaginations in the surface where adjacent wrinkles pack closely enough that they begin to coalesce, referred to as secondary folding. In a flat metal thin film, discontinuities produce a large effect in the resistivity of the film. Without wishing to be bound to any particular theory, we hypothesize that secondary folding in a wrinkled Au thin films creates an increase in electrical contacts, thereby circumventing these discontinuities and reducing the effective resistivity of the wrinkled thin film electrodes.

Moreover, the crumpled configuration of the conductor 108 allows for a great degree of extensibility when subject to strain. The conductor 108 is folded upon itself in the at-rest state and unfolds or unfurls when under strain to an elongate state without being subject to fracture. This mechanical integrity allows the conductor 108 to continue to function even when under strains that are severe for conventional thin film strain gauges.

Method of Forming High Strain Film Conductor

Figure 8:
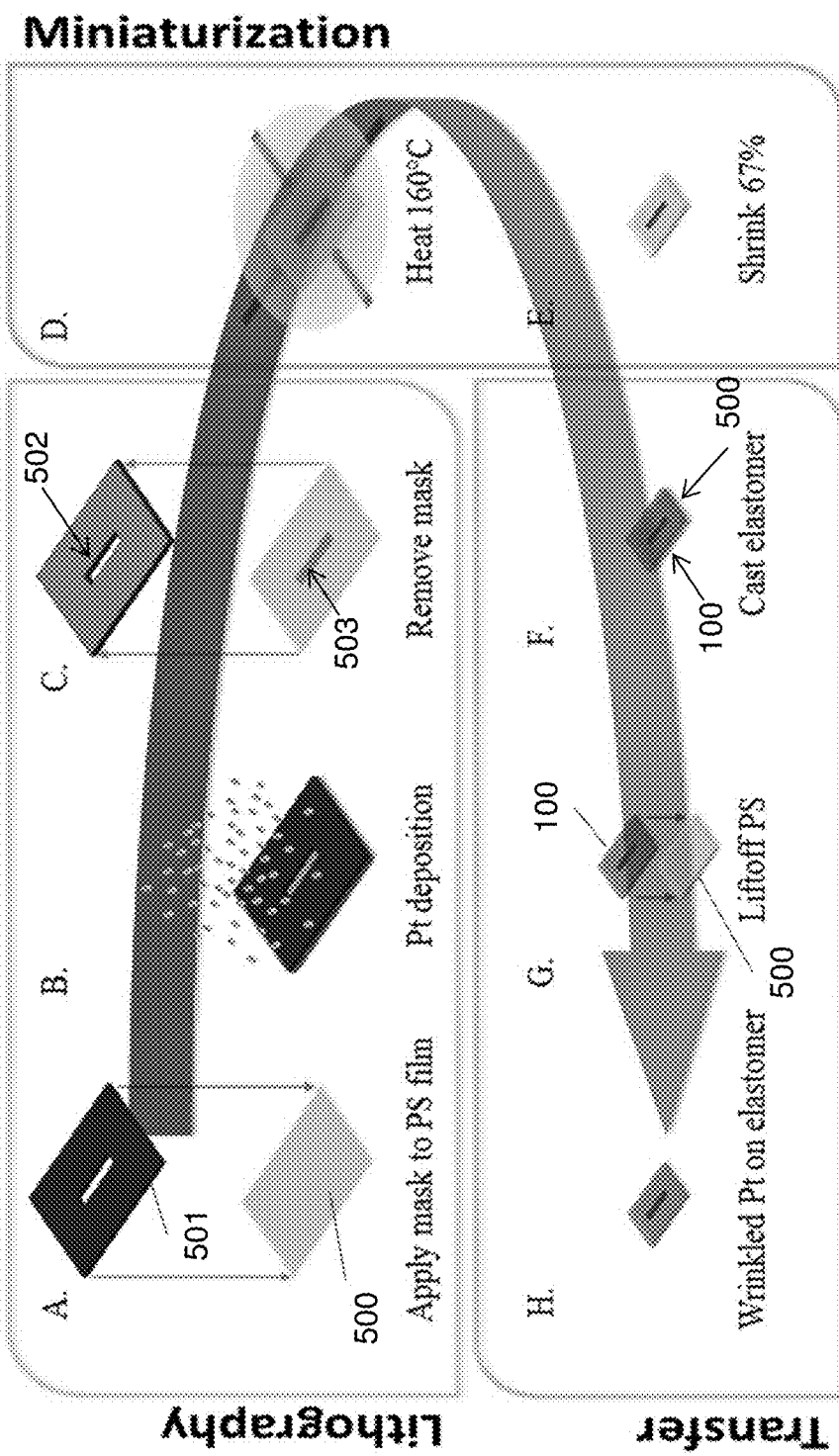
FIG. 8 illustrates a process for making and transferring a wrinkled metal thin film to an elastic material. The process can be separated into 3 sub-processes: Lithography (A-C), Miniaturization (D, E), and Transfer (F-H).
Figure 10:
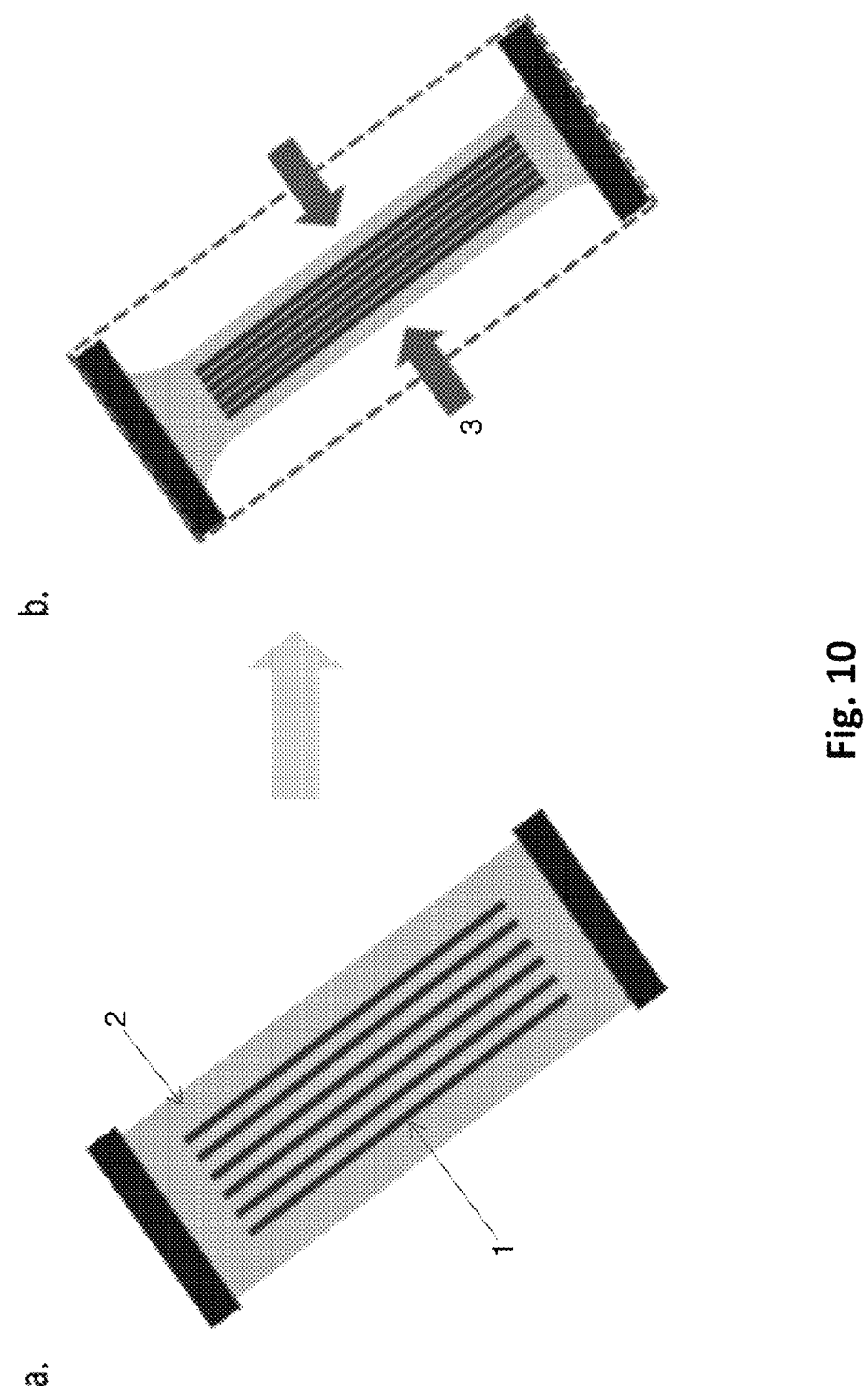
FIG. 10. Schematic of CNT densifying on polyolefin. (a) CNTs (1) on shape memory polymer, e.g., polyolefin (2), before shrinking. (b) CNTs on polyolefin after uniaxial shrinking (3) via heat resulting in densification.
Figure 11:
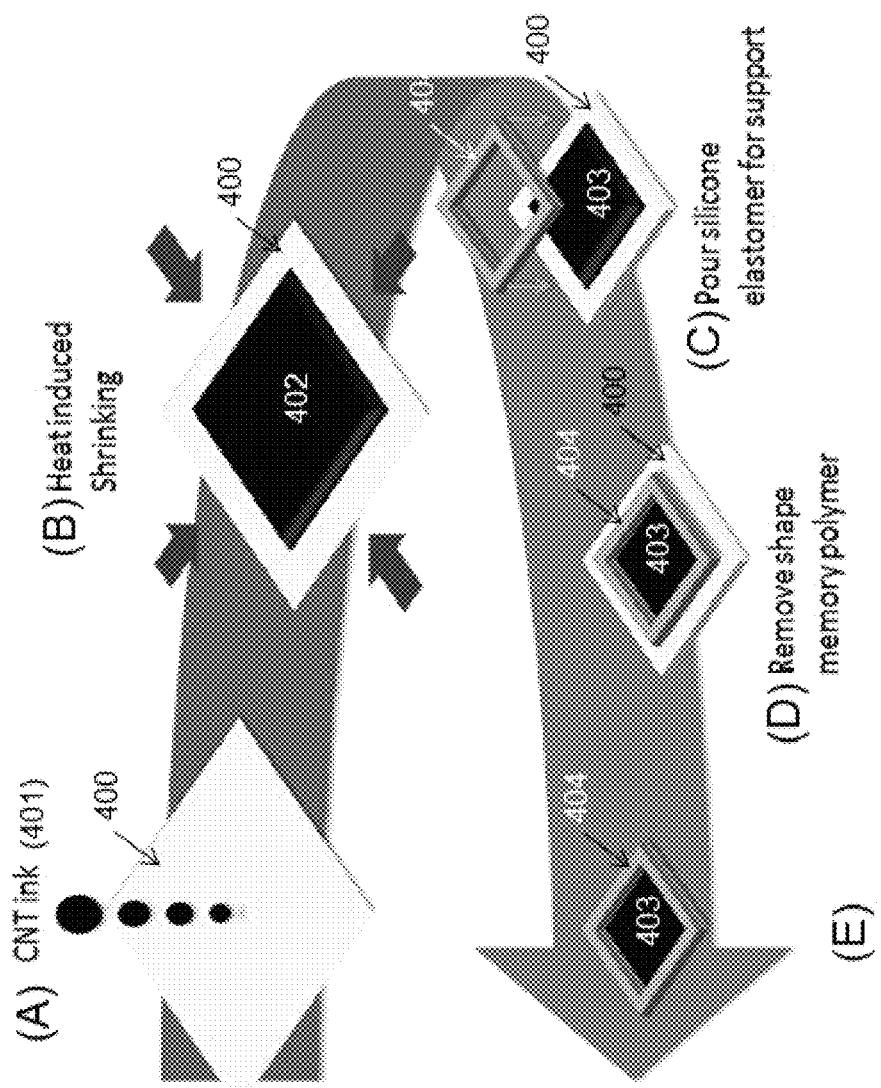
FIG. 11. Process flow for forming a wrinkled carbon nanotube (CNT) thin film. (A) Carbon nanotube ink is deposited on a flexible substrate; (B) Heat induced shrinking of preshrunk layer of CNT, resulting in shrunk CNT thin film; (C) Elastomer poured and cast onto shrunk CNT thin film; (D) Remove flexible substrate from shrunk CNT thin film and elastomer support; (E) shrunk CNT thin film with elastomer support.

The micron-scale configuration discussed above can be provided by any suitable method. FIG. 8 shows one technique that involves exploiting a heat-shrink material. In FIG. 8, panel (A) the polystyrene shrink film is masked. In panel (B) a metal thin film is deposited. In panel (C), the mask is removed and in panels (D and E) the shrink film is heated to 160° C., shrinking the metal patterned polymer by about 67% by surface area. In panel (F), a flexible polymer, such as ECOFLEX 30™ is spin coated onto the shrunken sample and cured. In panel (G), a series of solvent baths or other separation technique is used to lift off the polystyrene, resulting in the wrinkled metal thin film transferred onto the silicon elastomer (panel H). In some embodiments, a polymeric sheet 500 of suitable heat-shrink characteristics is placed adjacent to a mask 501 configured to block regions of the polymeric sheet 500. This may be followed by a step of depositing a conductive structure 503 on the polymeric sheet 500 at regions exposed through the mask 502. After the conductive structure 503 is formed, the mask 501 can be removed. The process then follows with shrinking the polymeric sheet 500 with the conductive structure 503 patterned on its surface by heating. The metal-patterned polymer may be reduced in size with regard to surface area by 5%, 10%, 15%, 20%, 25%, 30%, 35%, 40%, 45%, 50%, 55%, 60%, 65%, 70%, 75%, 80%, 85%, 90% or 95%. Thereafter, the conductive structure 503 is transferred to a flexible substrate.

The conductive structure 503 can be deposited by any method, for example by air brushing or by electrospray of a material onto a surface. In some embodiments, the conductive structure 503 comprises any conductive metal. In some embodiments, the metal conductive structure is a thin metal film. In some embodiments the metal is selected from the group consisting of Cu, Ag Au, and Pt. In some embodiments, the polymeric sheet 500 may be a shape-memory (e.g., a shrink-wrap) polyolefin (P0) film. The shrinking step may performed at a temperature of about 100° C., 110° C., 120° C., 130° C., 140° C., 150° C., 160° C., 170° C., 180° C., 190° C., 200° C., 210° C. or 250° C. Among the materials that are well suited for heat-shrink processing is polystyrene.

Sensor Assembly Including a High Strain Film Conductor and Flexible Medium

The foregoing method forms a suitable conductive structure for a sensing apparatus. However, many heat shrink materials are more rigid than would be preferred for some applications. For example, it may be desirable to configure the sensing apparatus with as little shape-retaining characteristics as possible. It may be desired to permit the sensing apparatus to drape over a natural structure such as a joint or an expanse of skin. It may be desirable to couple this highly conformal sensing apparatus to a platform that will retain mechanical integrity during continuous use of an hour or more, up to two hours, or even a period of twenty-four hours or more. Thus, it may be desired to transfer the conductive structure to a flexible substrate. The flexible substrate can provide mechanical backing for the highly conformal sensing apparatus while allowing it to retain sufficient flexibility to reliably and repeatedly detect movement.

In one method, it is desired to transfer the conductive structure 503 to an elastomeric polymer. One technique involves cast molding an elastomeric polymer support 504 onto the same surface of a heat-shrunk polymeric sheet 500 upon which the conductive structure 503 is deposited (see FIG. 8, step F). The cast molding can involve preparing the elastomeric material in liquid form and dispensing it onto the surface upon which the conductive structure 503 is deposited. The liquid elastomeric polymer is permitted to solidify. Thereafter, the conductive structure 503 is sandwiched between an elastomeric layer of the support 504 and the heat-shrunk polymeric layer 500. Thereafter, the heat-shrunk polymeric layer 500 optionally is removed (see FIG. 8, step G), leaving the conductive structure 203 on the surface of the elastomeric layer of the support 504.

Metal patterns can be fabricated directly on polydimethylsiloxane (PDMS) by using stencil masks or photolithography; however, there are some limitations to these methods, such as being restricted to patterns with only simple structures, contamination by wet chemicals and cracks because of a large mismatch in the coefficient of thermal expansion of PDMS and that of metals. More importantly, after direct metal patterning on PDMS, high-temperature processes (e.g., annealing) cannot be applied to the sample because of the low melting point of PDMS. Instead of direct-metal patterning on PDMS, it has been reported that metal patterns can be prepared on rigid substrates (e.g., Si or glass wafer); and then the patterns can be transferred to receiver substrates (e.g., PDMS).

For flexible electronics, a strong bond between the metal and the PDMS substrate is very important in order to fabricate a robust and reliable device that is able to endure the stresses induced by the bending of the substrates. If the metal patterns do not bond strongly to the PDMS surface, they can be damaged or lifted off easily by the applied voltage or fluidic pressure. For example, evaporated Au does not adhere to PDMS due to the weak interaction to PDMS.

An adhesion layer is optionally placed between the conductive structure and the elastomeric layer. In some embodiments, Pt is deposited first on a polymeric material, such as polystyrene (see FIG. 8, step B). This may be followed by deposition of a thin layer of Au, which forms metallic bonds with the Pt Any silane molecule may be used as a surface adhesion molecule. For example, when silicon (e.g., polydimethylsiloxane (PDMS)) is used as the elastomer, the thin film of Au can be covalently bonded to the silicon elastomer using 3-mercaptopropyl) trimethoxysilane (MPTMS) as a molecular adhesive (Byun I. et al. 2013 *J Micromech Microeng* 23(8): 1-10, incorporated herein by reference). Following heat-shrinkage of the polymeric material (see FIG. 8, steps D and E), the gold surface is treated with 3-mercaptopropyl) trimethoxysilane (MPTMS), which functions as a molecular adhesive in bonding the conductive layer to the silicon elastomer. When the wrinkled, conductive layer attached to the elastomer is lifted off of the heat-shrunk polymer, the Pt is exposed.

Several methods to promote adhesion between metal patterns and PDMS are known. The first is to use Ti or Cr as an adhesion interlayer and then activate and hydroxylate the respective surfaces of the metal and PDMS by oxygen plasma or UV/$O_3$ exposure in air. Conformal contact of two hydroxyl (—OH) groups on Ti (5 nm) surface (titanol) and hydroxylated PDMS surface (silanol) by oxygen plasma treatment results in permanent Ti—O—Si bonds. Cr (3 nm) and $SiO_2$ (30 nm) can be deposited on Au electrodes and delivered to PDMS, which is surface activated by exposure to UV/$O_3$, to form Si—O—Si linkages. Similarly, the adhesion can be enhanced between the metal electrodes and the PDMS by thermal curing a prepolymer of PDMS on Au electrodes with Ti interlayer (5 nm). However, using Cr or Ti as an adhesion layer can deteriorate the optical and electrochemical performance of the device, nor are these elements suitable for bio-applications. However, using a molecular adhesive that bonds to both the metal and PDMS may be an alternative to avoid the problems caused by additional metallic interlayers.

For a molecular adhesive, (3-mercaptopropyl) trimethoxysilane (MPTMS), as a self-assembled monolayer (SAM), is versatile because of the different functionality of its two terminal groups. Simultaneously, the three methoxy (—$OCH_3$) functional end groups can bind to oxide surfaces, while the thiol (—SH) functional head group can bind to metals. MPTMS has been used for the transfer of Au films to PDMS. Au patterns treated with MPTMS can bond to PDMS by pouring a PDMS prepolymer onto the Au patterns and subsequent thermal curing or bringing the Au patterns to PDMS whose surface was activated by exposure to UV/$O_3$. Not only Au, but also PDMS can be treated with MPTMS. This PDMS treated with MPTMS can bond with Au patterns by bringing them into contact Other alternative polymer elastomers may be used, such as urethane. For other types of polymer elastomers, corresponding adhesion methods are utilized.

The presence of an adhesion layer that adheres the conductive structure to the elastomeric substrate can significantly improve the dynamic range of a sensor. Without wishing to be bound to any particular theory, this may be because the conductive structure is anchored to the elastomeric substrate, allowing it to stretch in response to strain and to retract to its original conformation upon relaxation of the strain. In some embodiments, the dynamic range of a sensor containing an adhesion layer interposed between the conductive structure and the elastomeric layer is 10%, 20%, 30%, 40%, 50%, 60%, 70%, 80%, 90%, 100%, 110%, 120%, 130%, 140%, 150%, 160%, 170%, 180%, 190% or 100% greater than a comparable sensor that lacks an adhesion layer.

Further steps may involve encapsulating the conductive layer. Further steps may involve coupling the conductive layer with other devices, such as may be used to direct current through the conductive layer, to receive current directed through the conductive layer, to store and/or transmit data regarding the resistance or changes in resistance of the conductive layer, to provide one or more signals to the user or patient or for other purposes.

Carbon Nano-tube Based Sensors and Processing

Carbon nanotube (CNT)-based sensors comprise a condensed, conductive layer of carbon nanotubes. Applications for CNTs on elastic substrates, including pressure sensors, are described by Lipomi et al. (2011 "Skin-like pressure and strain sensors based on transparent elastic films of carbon nanotubes" *Nature Nanotechnology* 6: 788-792). CNT-PDMS based sensors are used for applications including speech recognition and pulse detection (Wang et al. (2014 "Silk-Molded Flexible, Ultrasensitive, and Highly Stable Electronic Skin for Monitoring Human Physiological Signals" *Advanced Materials* 26: 1336-1342). The conductivity of a CNT-based sensor can be greater than the conductivity of a metal film-based sensor, e.g., 5, 10, 15, 20, 25 or 50 times higher.

FIG. 7 shows a process flow for forming a wrinkled carbon nanotube (CNT) thin film. In panel A, carbon nanotube ink 401 is deposited on a flexible substrate 400. In panel B, heat induced shrinking of preshrunk layer of CNT 402 results in shrunk CNT thin film 403. In panel C, elastomer 404 is poured and cast onto shrunk CNT thin film 403. In panel D, flexible substrate 400 is removed from shrunk CNT thin film 403 and elastomer support 404. Panel E shows shrunk CNT thin film 403 with elastomer support 404.

Sensors Having a One Dimension Nanostructure

In some embodiments the sensor includes one-dimensional (1D) nanostructures, such as those depicted in FIGS. 10-14. Such sensors can include one or more of nanotubes, nanofibers, nanowires, and rods. A class of nanostructures includes nanoconductors. A nanostructure is said to be one dimensional, for example, if it much longer in one direction than in other directions perpendicular to the long direction, for example having a diameter on the order of a nanometer ($10^{-9}$ meters) and a length larger than 10 nm, larger than 50 nm, larger than 80 nm, larger than 90 nm or larger than 100 nm. Nanotubes include carbon nanotubes, for example. A nanowire is a nanostructure, with the diameter of the order of a nanometer ($10^{-9}$ meters). A nanostructure can be defined as the ratio of the length to width being greater than 1000. Many different types of nanowires exist, including superconducting (e.g., YBCO), metallic (e.g., Ni, Pt, Au), semiconducting (e.g., Si, InP, GaN, etc.), and insulating (e.g., $SiO_2$, $TiO_2$). As disclosed herein, a 1D nanostructure is densified and aligned to produce an effective conductor, which may be configured as a thin film.

Cost-effective technologies disclosed herein provide a process to highly densify and align 1D nanostructures, such as CNTs, to improve its conductivity using shrink technology. In some embodiments, this is done by depositing a thin film of CNTs on the surface of a shape memory polymer, such as polyolefin. Preferably the polymer is a chemically resistant shape memory polymer. The process includes uniaxially, biaxially, or multiaxially shrinking the polymer by subjecting it to heat. Increasing the density and alignment of CNTs improves the conductivity of the assembly for strain gauge sensors and other applications that use CNTs. Other applications include batteries and chemical sensors.

We demonstrate that biaxial or multiaxially shrinkage of a CNT thin film produces wrinkled structures. As noted above, shrinking of metal films can produce wrinkling in the film. More generally, this wrinkling occurs if stiffness mismatch is provided between a substrate layer and a layer to be wrinkled or crumpled. We have found that a CNT thin film also produces wrinkling. It is believed that the total amount of van der Waals force between each individual CNTs is strong enough to create a stiff thin layer consequently wrinkling after biaxial or multiaxial shrinkage. This wrinkling phenomenon can be produced on shape memory polymers that shrink. We have also shown that the CNT thin film can be transferred onto a soft silicone substrate after removal of the shape memory polymer.

In some embodiments, the thin film of CNTs is shrunk by heating to a temperature of about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C., or about 250° C. or a range bounded by any two of the preceding numerical values.

A polyolefin is any of a class of polymers produced from a simple olefin (also called an alkene with the general formula $CnH_{2}n$) as a monomer. For example, polyethylene is the polyolefin produced by polymerizing the olefin ethylene. An equivalent term is polyalkene.

In some embodiments, the CNTs are dispersed in a solution of an organic solvent, such as chloroform, prior to deposition on a shape memory polymer. Other non-limiting examples of organic solvents include benzene, toluene and phenyl ethyl alcohol or other solvents (Li et al. 2012 "Dispersion of Carbon Nanotubes in Organic Solvents Initiated by Hydrogen Bonding Interactions" AIChE Journal 58: 2997-3002; Dumonteil et al. 2006 "Dispersion of carbon nanotubes using organic solvents" J Nanosci Nanotechnol 6(5): 1315-1318; and Ausman et al. 2000 "Organic Solvent Dispersions of Single-Walled Carbon Nanotubes: Toward Solutions of Pristine Nanotubes" J Phys Chem B 104: 8911-8915).

Densifying CNTs in a sensor application increases the sensitivity of the sensor, proportional to the degree to which a shape memory polymer shrinks. For example, a 95% reduction in area by shrinking on a polyolefin enables a much higher responsiveness. In some embodiments, a stretch senor or a strain gauge device, containing densified CNTs, has a correspondingly lower electrical resistance upon densification of the CNTs. In some embodiments, the resistance of a film upon densification is reduced to about 100 kfl. In some embodiments, the resistance of a film upon densification is reduced to about 10 kfl, about 50 kfl, about 100 kfl, about 150 kfl, about 200 kfl, about 250 kfl, about 300 kfl, about 350 kfl, about 400 kfl, about 450 kfl, about 500 kfl, about 550 kfl, about 600 kfl, about 650 kfl, about 700 kfl, about 750 kfl, about 800 kfl, about 850 kfl, about 900 kfl, about 950 kfl, about 1000 kfl, about 1100 kfl, about 1200 kfl, about 1300 kfl, about 1400 kfl or about 1500 kfl or a range bounded by any two of the preceding numerical values. A low resistance film allows the development of highly sensitive devices that were previously not feasible based on previously existing technologies.

In some embodiments, the density amplification of the CNTs relative to an initial density upon application of the CNTs to a shape memory polymer is an increase of about 100%, about 150%, about 200%, about 250%, about 300%, about 350%, about 400%, about 450%, about 500%, about 550%, about 600%, about 650%, about 700%, about 750%, about 800%, about 850%, about 900%, about 950%, about 1000%, about 1100%, about 1200%, about 1300%, about 1400% or about 1500% or a range bounded by any two of the preceding numerical values.

CNT density can be measured by a light transmittance test. In some embodiments, the CNT density results in light transmittance values of between about 30 to about 90%. In some embodiments the light transmittance is about 30%, about 35%, about 40%, about 45%, about 50%, about 55%, about 60%, about 65%, about 70%, about 75%, about 80%, about 85% or about 90% or a range bounded by any two of the preceding numerical values.

Face-to-Face Designed CNT Pressure Sensors

Figure 16:
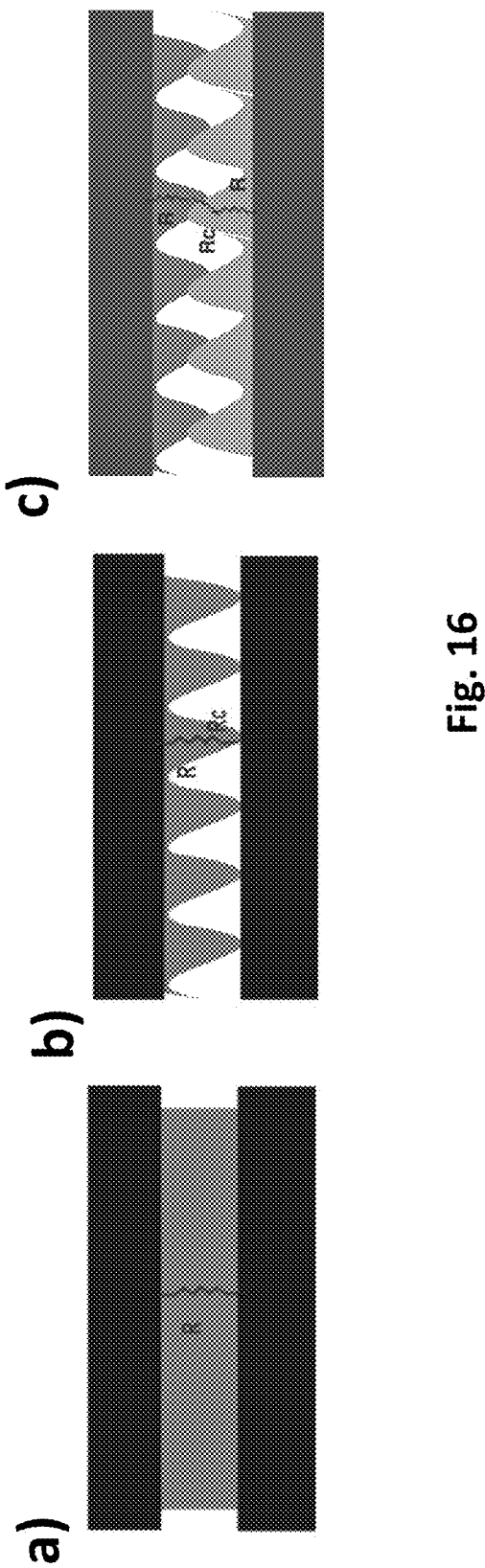
FIG. 16 illustrates a) planar, b) single wrinkled CNT, and c) face to face type pressure sensor designs.
Figure 17:
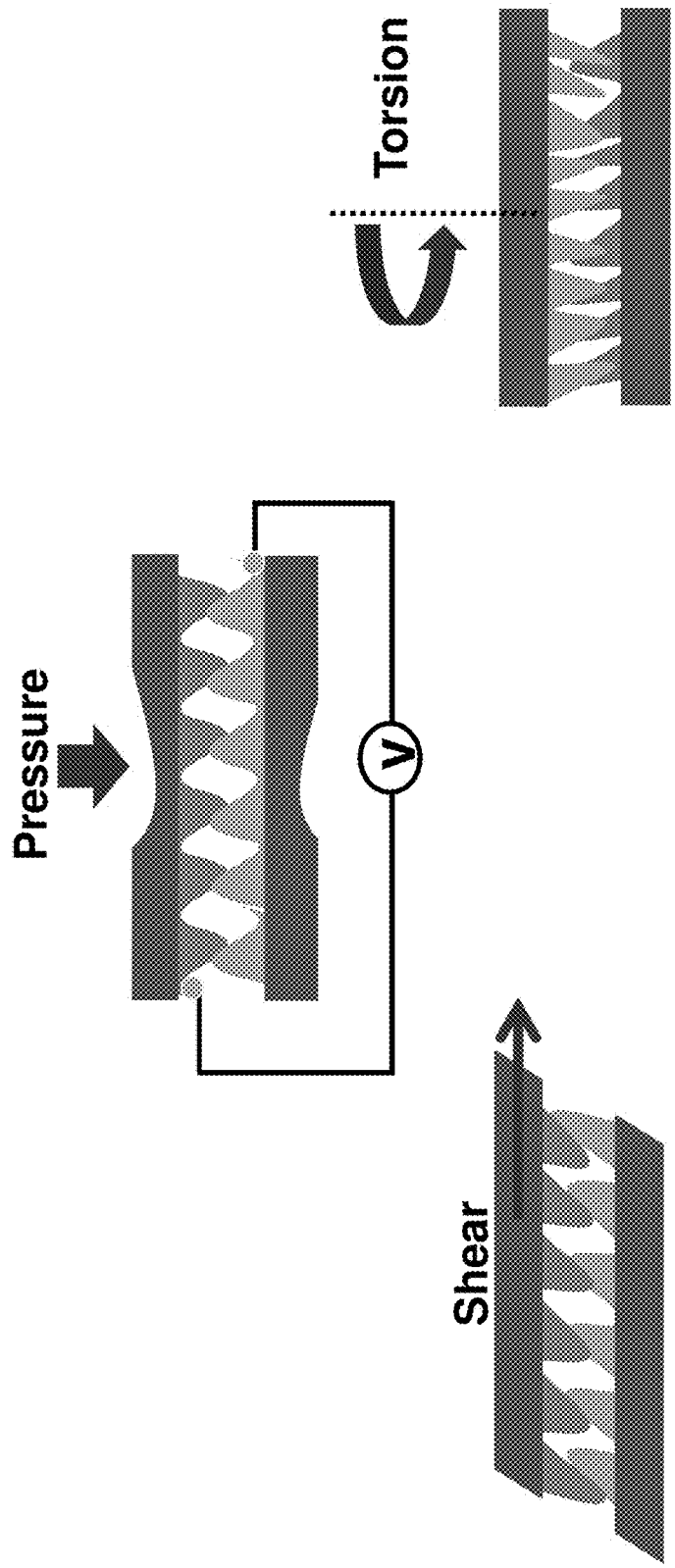
FIG. 17 shows schematic illustrations of pressure, shear and torsion loads and their possible geometric distortions of wrinkled structures in face-to-face designed pressure sensors.

Wrinkled CNT thin films have two novel applications, including resistance-based and capacitive pressure sensing. With regard to response/relaxation times, planar films are limited by the elastic behavior of a CNT network. Face-to-face type sensors show a rapid response time due to immediate pressure-induced surface deformation of the wrinkles. They also exhibit low temperature dependence. (Interfiller distance changes during the thermal expansion of the composite). FIGS. 16 and 17 illustrate how the wrinkled topography of CNT thin films contribute to resistance-based and capacitive sensing. By combining 2 sensing modalities in a face-to-face configuration, motion is measured both in normal (perpendicular to a plane of a sensor) and in transverse directions, e.g., resulting in shear or torsion.

Resistance-Based Pressure Sensors

Resistance-based pressure sensors (also referred to as piezoresistive percolating sensors) are fabricated by transferring a wrinkled CNT thin film (~30 nm thick) onto a thin PDMS substrate (~300 um thick). Two CNT-PDMS substrates are then placed together so that the CNT wrinkles are in contact. This configuration allows CNT wrinkles to be encapsulated by the PDMS. Electrodes are attached on opposite ends of the sensor. As applied pressure is increased, the contact points between the CNT wrinkles increases, and as a result, resistance decreases through the sensor.

Capacitance-Based Pressure Sensors

For capacitive-based sensors, a dielectric layer (such as a thin film of PDMS) is placed between the wrinkled CNT faces. As applied pressure increases, the dielectric layer is compressed so that the distance between the two wrinkled CNT conductors decreases, and a resulting capacitance increases.

Example Applications of Wrinkled CNT Structures

1. Flexible Devices

Wrinkled CNT thin films can be incorporated into flexible devices, such as in sensor apparatuses, including strain gauges. As noted above, the CNT thin films can form the sensing component of the sensor apparatus 100. An advantage of using wrinkled films in flexible devices is the ability to stretch out the wrinkles produced from shrinking. Depending on the shape memory polymer used, it is theoretically possible to stretch out to the original, pre-shrinkage dimensions.

Various applications benefit from strain gauges that can undergo large strains and still produce repeatable, predictable outputs. For example, it is desired that such a strain gauge or other sensor apparatuses can be mounted on a flexible substrate and connected to surfaces that are highly curved, mobile and/or repeatedly flexed during the duty cycle of the strain gauge or sensor apparatus. It would be useful for a sensor apparatus herein to be wearable to enable various health or physiological condition monitoring applications, such as for monitoring fetal or maternal health and more comprehensively progress of a pregnancy.

2. Piezoresistive and Capacitive Sensors with Wrinkled CNT Structures

Wrinkled CNT thin films can also be used in the fabrication of piezoresistive and capacitive sensors (Limpomi, D. J.; Vosgueritchian, M.; Tee, B. C-K.; Hellstrom, S. L.; Lee, J. A.; Fox, C. H.; Bao, Z. Nature Nanotech. 2011, 6, 788-792, incorporated herein by reference). As such CNT thin films can be used to provide a capacitive sensor for monitoring fetal or maternal health and more comprehensively progress of a pregnancy. Elastic conductors are advantageous components for use in electronic and optoelectronic devices that facilitate human interaction and biofeedback, such as interactive electronics, implantable medical devices and robotic systems with human-like sensing capabilities. The availability of conducting thin films with these properties provides a basis for the development of skin-like sensors that stretch reversibly, sense pressure, bend into hairpin turns, integrate with collapsible, stretchable and mechanically robust displays and solar cells, and also wrap around non-planar and biological surfaces such as skin and organs.

Advantages

Multiple devices are currently needed to monitor different vital signs. The wearable monitors disclosed herein combine more than one vital sign measuring function into one device in some embodiments. Also, traditional vital signs monitors also require clinician operation and hand recording measurements, but the disclosed monitors measure and record vital signs automatically via integrated wireless communication, e.g., near field transmission or Bluetooth, for more efficient health care. The monitors can be wireless and wearable, e.g., to be worn conveniently on the wrist or at another location with superficial arteries. The monitors can provide immediate data during medical emergencies, and can also provide continuous monitoring for better observation, diagnosis, and care for long term patients. The sensor(s) 16, materials of the self-supporting band 4 and components of the electronics module 20 preferably are low cost, enabling the monitors to be a good alternative to expensive traditional vital signs monitoring devices. If the electronics module 20 is made re-usable it could be mated with bands 4 having different sensor arrays, e.g., one or more than one sensor 16, sensors for sensing different conditions.

Example 1

Radial Artery Pulse Rate Measurement

Figure 18:
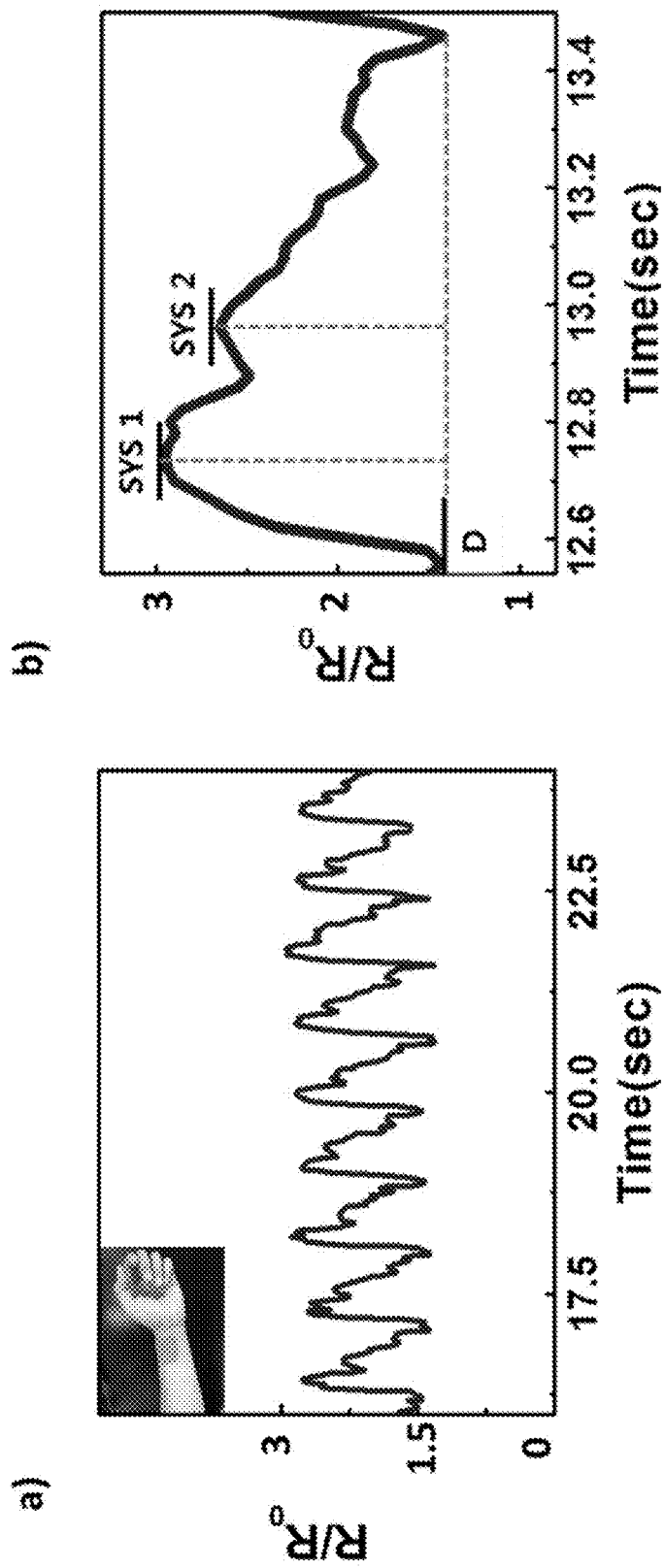
FIG. 18 shows pulsatile blood flow detection. (a) Change in Resistance vs. time showing pulsatile blood flow. (b) Expanded view of a single pulse wave. The sensor detects a first systolic peak (SYS1), second systolic peak (SYS2) and a diastolic peak (D).

Pulsatile blood flow is detected by placing our flexible pressure sensor on the radial artery of the wrist, demonstrating pulsatile blood flow detection (FIG. 18, panel (a). The pulsatile blood flow pressure from the wrist pushes against the sensor, consequently reducing the electrical resistance between the face-to-face wrinkled thin films. The sensor is able to distinguish systolic (SYS) and diastolic (D) phases of the pulsatile blood flow. Using this information, the augmentation index (AI) may be calculated. AI is a useful parameter that has been associated with vascular aging (Kohara, K. et al. 2005 "Radial augmentation index: A useful and easily obtainable parameter for vascular aging" *Am J Hypertens* 18: 14-17; and Chirinos, J. A. et al. 2011 "Ethnic differences in arterial wave reflections and normative equations for augmentation index" *Hypertension* 57: 1108-1116). Referring to FIG. 18, panel (b), a first systolic peak (SYS1), a second systolic peak (SYS2), and a diastolic peak (D) are observed. By measuring these peaks, it is possible to calculate the AI where AI=(SYS2−D)/(SYS1−D).

Example 2

Respiration Rate Measurements

The flexible pressure sensor is attached to a chest or abdomen of a subject A characteristic respiration signal is obtained and evaluated over time to determine respiration rate.

Example 3

Estimation of Central Aortic Pressure Waveform by Mathematical Transformation of Radial Tonometry Pressure Central aortic pressures and waveform convey important information about cardiovascular status, but direct measurements are invasive. Peripheral pressures are measured non-invasively. Although they often differ substantially from central pressures, they may be mathematically transformed to approximate the latter (Chen et al. 1997 Circulation 95:1827-1836).

Radial Artery Pressure Recording

Radial pressure waves are recorded with the use of a wrist-mounted vitals band device as disclosed herein. Pressure recordings are digitized at 200 Hz and stored for off-line analysis. Two-minute steady-state data recordings are made in each subject Estimation of Transfer Functions Transfer functions (TF) between aortic pressure and radial pressure signals are derived in each patient by the linear ARX model (Ljung L. System Identification: Theory for the User. 1st ed. Upper Saddle River, N.J.: Prentice Hall; 1987). The ARX linear model describes the properties of a system on the basis of its immediate past input and output data as:

$$T(t)=-a_1T(t-1)-a_2T(t-2)-\ldots-a_{na}T(t-na)+b_1P(t-1)+\ldots+b_{nb}P(t-nb) \quad (1)$$

where T(t) and T(t−I) [I=1, 2 . . . na] are present and previous output (radial tonometer) discrete measurements, respectively, and P(t−I) are previous input (aortic pressure) discrete measurements. $a_1$, $a_2$, $a_{na}$ and $b_{nb}$ are parameters of the model and na and nb represent a number of previous input-output values used to describe the present output This methodology yields more statistically stable and thus reliable spectral estimates from limited data compared with nonparametric (Fourier transform) approaches. Mean individual patient TFs and their variances are evaluated by three to five TFs estimated from separate steady-state data sequences ($ITF_{ss}$).

Model Order Selection

The model order for this study was set to be [10,10], i.e., 10 "a" coefficients and 10 "b" coefficients are determined for each TF estimate. The minimal model order is set to be [5,5] to achieve a similar spectral estimate as given by nonparametric methodology (Fourier transform) during steady state. The maximal model order is set at [20,20] on the basis of calculating the Akaike Information Criterion, which measures the estimation performance against the model order. The actual model order for the estimation process is selected by testing whether a higher model order yielded a change in the spectral estimate that was larger than the SD of the estimate. This approach is justified because increasing the model order, although resulting in better fit of the measured data, usually increases the variance of the estimate. Determination of the smallest model order with sufficient spectral resolution is essential to enable reliable estimation based on short data sequences during hemodynamic transients.

Comparison with Fourier Transform Estimation

Parametric models can be compared with nonparametric methods, e.g., TF estimation with the Fourier transform. When the same data set is used, the parametric and nonparametric estimates produce similar results, although the parametric methodology provide a smaller variance of the estimate. The variance of the Fourier-derived spectrum is similar to that of the ARX-derived spectrum only when the larger data set was used.

Direct and Inverse TFs

Direct TFs that correspond to the physiological system are estimated with the aortic pressure used as input and the radial tonometer signal as output. To enable reconstruction of the aortic pressure from the radial tonometer signal, an inverse TF is directly derived from the direct TF (Equation 1) as follows:

$$P(t-1)=-b_2/b_1P(t-2)-\ldots-b_{nb}/b_1P(t-nb)+1/b_1T(t)+a_1/b_1T(t-1)+\ldots+a_{na}/b_1T(t-na) \quad (2)$$

Evaluation of Reconstructed Aortic Pressure Waves at Steady State

For each subject, two reconstructed steady-state aortic pressure waves are derived by applying the inverse generalized steady-state transfer function ($GTF_{ss}^{-1}$) and inverse individual steady-state transfer functions ($ITF_{ss}^{-1}$) to steady-state data. Aortic, radial, and the two estimated aortic pressure waves are then signal averaged to generate four pressure waveforms for each cardiac cycle. Systolic, diastolic, and pulse pressures; total arterial compliance; and augmentation index (AI) are calculated from each ensemble of pressure waves and compared. Waveforms are phase aligned, and point-by-point differences and regressions are used to compare waves. Overall agreement between the radial, reconstructed aortic, and invasive aortic pressures are quantified by the sum of squares of these differences normalized to the number of data points.

An error-sensitivity test is applied to evaluate the impact of the radial pressure calibration inaccuracies on estimated central pressures. Because the most common inaccuracy is in the diastolic pressure measurement, radial pressures are modified so that the input diastolic blood pressures are increased or decreased by 15 mm Hg in steps of 5 mm Hg, with systolic pressure kept constant. The $GTF_{ss}^{-1}$ are then applied to this altered radial data, and the influence of calibration error on estimated aortic systolic pressure is determined.

Example 4

Fabrication of Wrinkled CNT Piezoresistive Pressure Sensors

Figure 12:
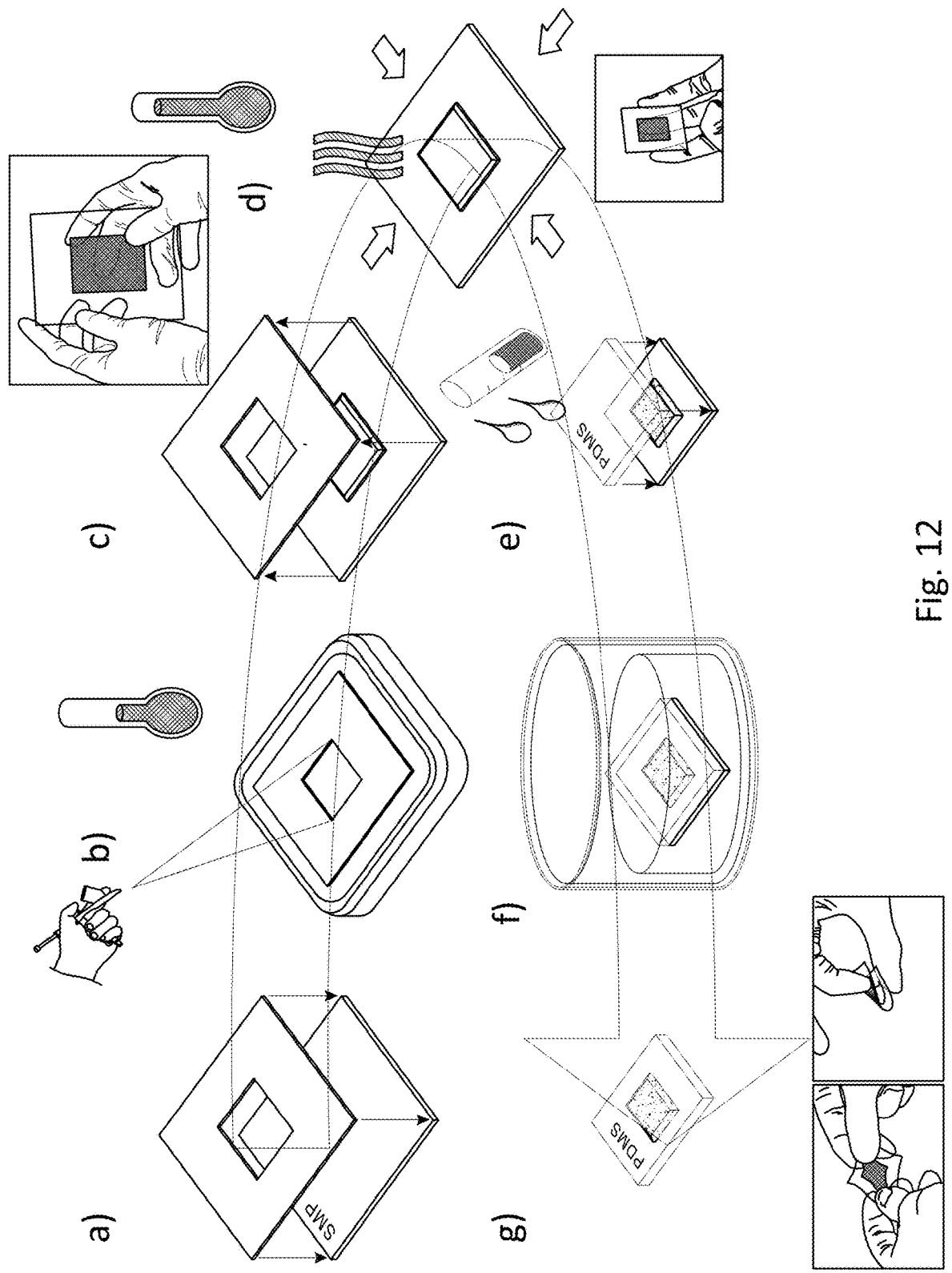
FIG. 12. Fabrication process flow of wrinkled CNT piezoresistive pressure sensors. (a) A shadow mask is mounted onto shape memory polymer (SMP). (b) A carbon nanotube (CNT) solution is deposited using a spray deposition. (c) The shadow mask is removed from SMP substrate. (d) The SMP substrate was heated to induce biaxial shrinking. (e) Polydimethylsiloxane (PDMS) was cured over the SMP substrate. (f) Organic solvents were used to transfer the wrinkled CNT thin film onto the PDMS substrate. (g) Final wrinkled CNT electrode for piezoresistive pressure sensing.
Figure 13:
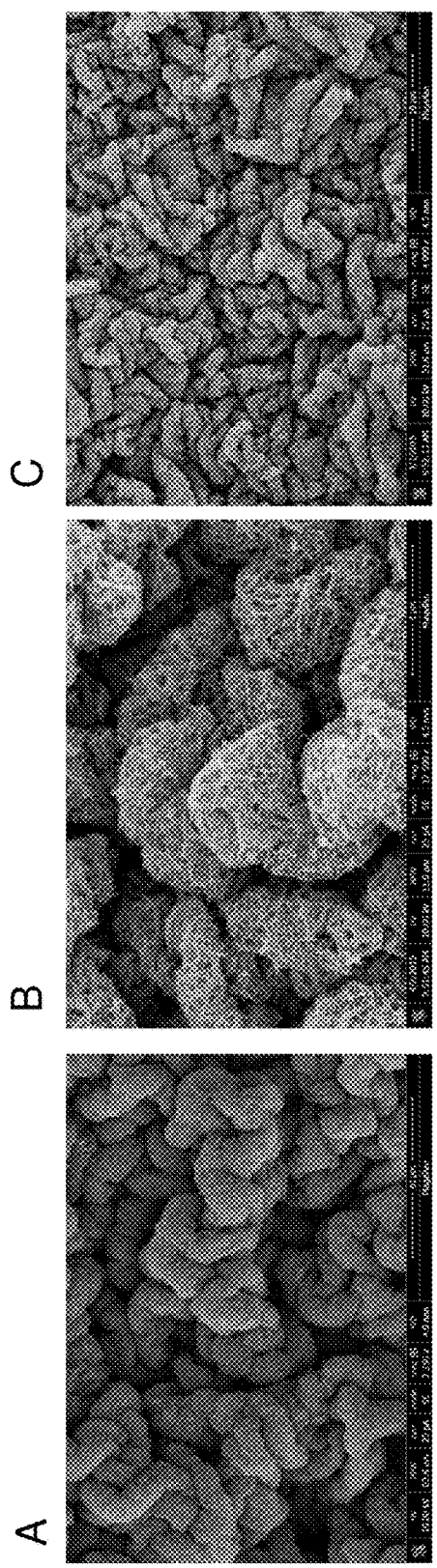
FIG. 13 show SEM images of wrinkled CNT thin film at various magnifications. (A) 3,250× magnification; (B) 17,500× magnification; and (C) 4,000× magnification.
Figure 14:
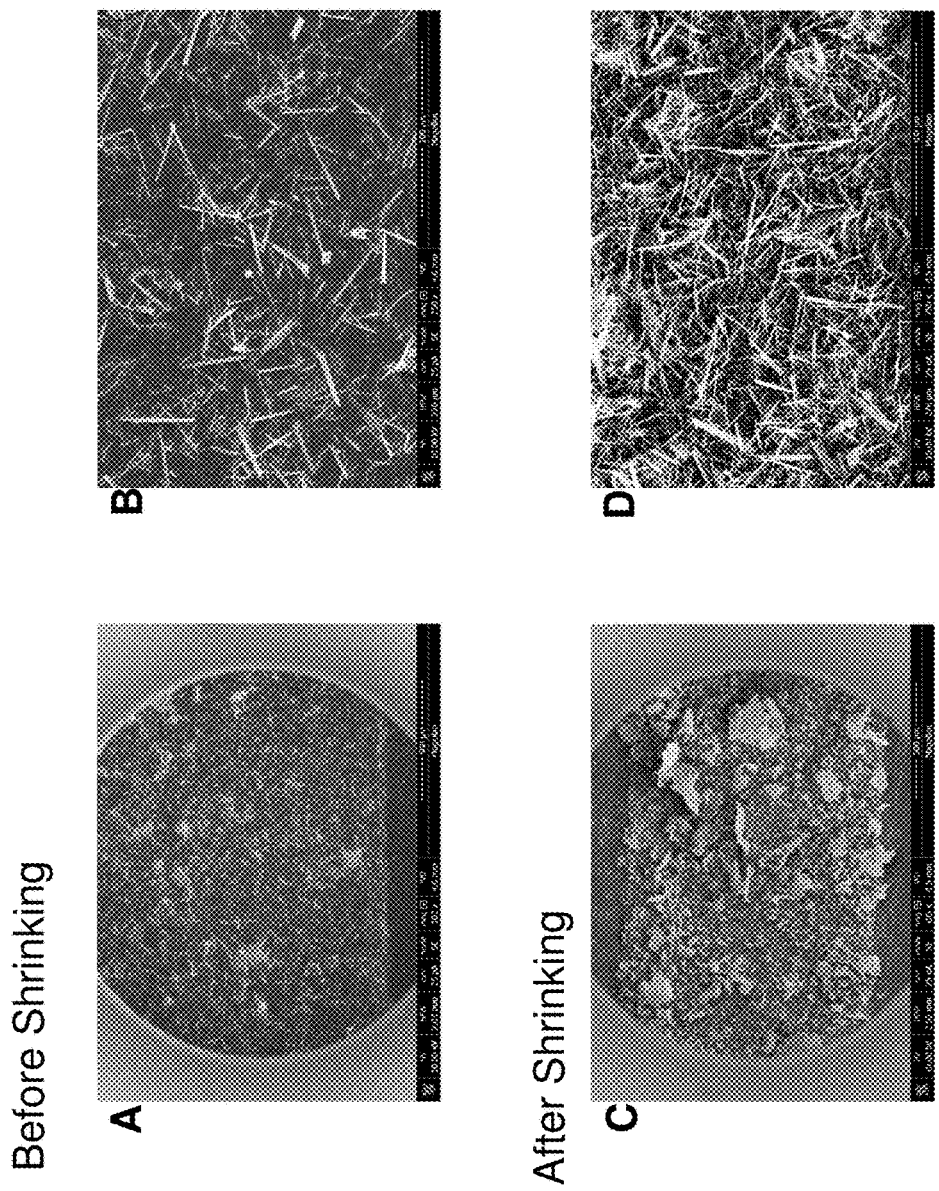
FIG. 14 shows SEM images of silicon nanowire films before and after shrinking. (A) Before shrinking, 102× magnification; (B) before shrinking, 750× magnification; (C) after shrinking, 103× magnification; (D) after shrinking, 750× magnification.
Figure 15:
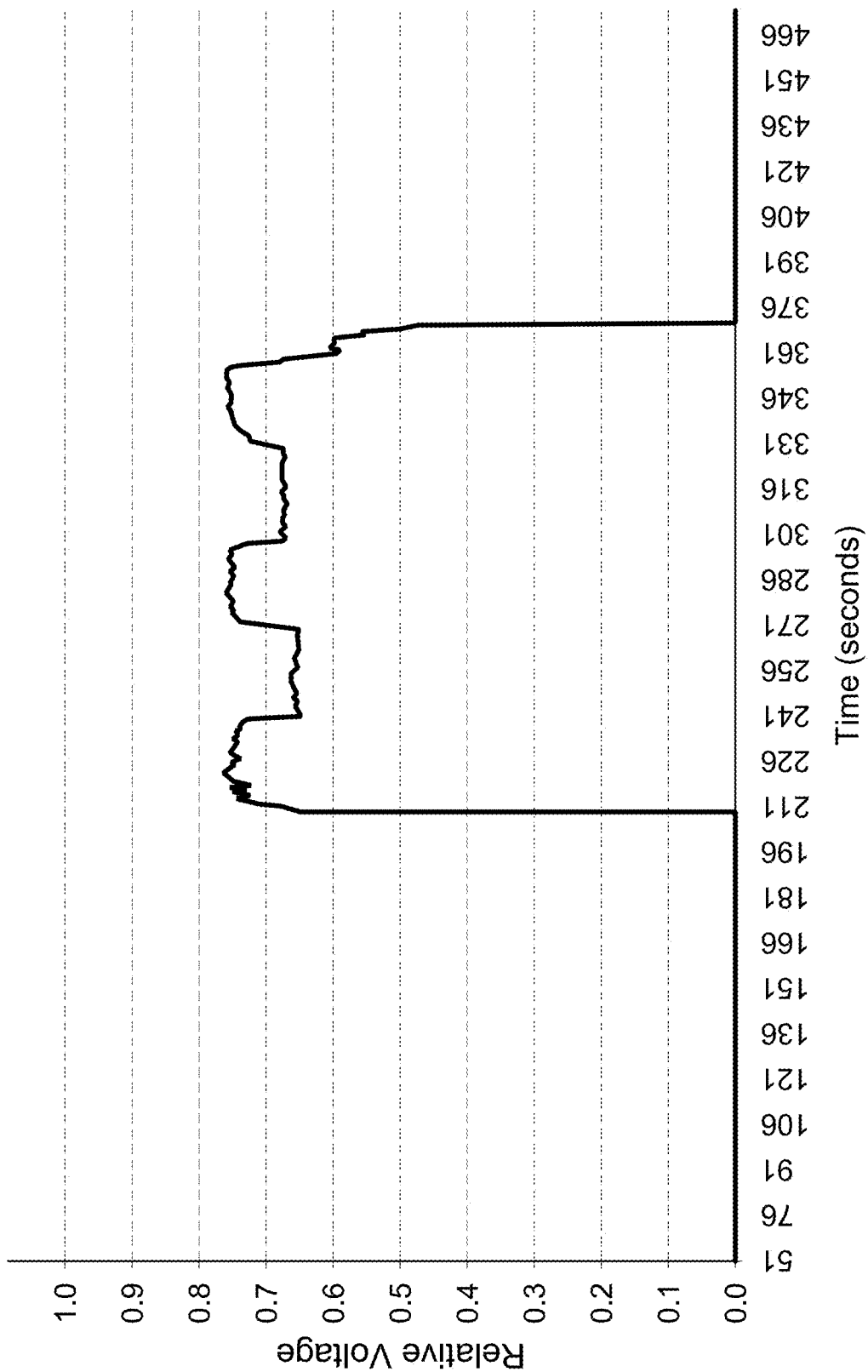
FIG. 15 shows output data when pressure is applied to a sensor. The x-axis represents time (seconds) and the y-axis represents a signal, e.g., measured as a voltage.

Fabrication process flow of wrinkled CNT piezoresistive pressure sensors. As shown in FIG. 12, panel (a), a shadow mask is mounted onto shape memory polymer (SMP). As depicted in panel (b), a CNT solution is deposited using a spray deposition. Referring to panel (c), the shadow mask is removed from the SMP substrate. As shown in panel (d), the SMP substrate is heated to induce biaxial shrinking. Referring to panel (e), Polydimethylsiloxane (PDMS) is cured over the SMP substrate. Organic solvents are used to transfer the wrinkled CNT thin film onto the PDMS substrate (f). A final wrinkled CNT electrode for piezoresistive pressure sensing is shown in panel (g).

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

All figures, tables, and appendices, as well as publications, patents, and patent applications, cited herein are hereby incorporated by reference in their entirety for all purposes.

What is claimed is:

1. A method of estimating a central aortic pressure waveform in a subject comprising:
    measuring a radial artery pressure waveform in the subject by using an apparatus comprising a wearable device comprising:
        (a) a supporting structure;
        (b) a sensor comprising a sensing modality selected from the group consisting of:
            a thin film strain gauge,
            a one-dimensional structure, and
            a planar structure; or
            two of the sensing modalities in a face-to-face configuration;
        (c) a processor; and
        (d) a transmitter;
    wherein the supporting structure is configured to press the sensor against a skin surface of a subject, wherein the sensor is configured to detect a biological metric of the subject, and wherein the processor is configured to quantify one or more signal(s) corresponding to the biological metric and the transmitter is configured to transmit the one or more signals to an external user system, and
    transforming the radial artery pressure waveform to a central aortic pressure waveform using a transfer function.

2. The method according to claim 1, wherein the transfer function describes the properties of a system on the basis of its immediate past input and output data.

3. The method according to claim 2, wherein the transfer function uses the relation:

$$T(t) = -a_1 T(t-1) - a_2 T(t-2) - \ldots - a_{na} T(t-na) + b_1 P(t-1) + \ldots + b_{nb} P(t-nb) \quad (1)$$

where $T(t)$ and $T(t-I)$ [$I=1, 2 \ldots na$] are present and are previous output (radial tonometer) discrete measurements, respectively, and $P(t-I)$ are previous input (aortic pressure) discrete measurements, $a_1$, $a_2$, $a_{na}$ and $b_{nb}$ are parameters of the model, and na and nb represent a number of previous input-output values used to describe the present output.

4. The method according to claim 1, wherein the wearable device further comprises:
    memory, and
    a battery.

5. The method according to claim 4, wherein the processor, memory, battery and transmitter are comprised within a housing disposed on an inner or an outer side of the supporting structure.

6. The method according to claim 4, wherein the transfer function describes the properties of a system on the basis of its immediate past input and output data.

7. The method according to claim 6, wherein the transfer function uses the relation:

$$T(t) = -a_1 T(t-1) - a_2 T(t-2) - \ldots - a_{na} T(t-na) + b_1 P(t-1) + \ldots + b_{nb} P(t-nb) \quad (1)$$

where $T(t)$ and $T(t-I)$ [$I=1, 2 \ldots na$] are present and are previous output (radial tonometer) discrete measurements, respectively, and $P(t-I)$ are previous input (aortic pressure) discrete measurements, $a_1$, $a_2$, $a_{na}$ and $b_{nb}$ are parameters of the model, and na and nb represent a number of previous input-output values used to describe the present output.

* * * * *